United States Patent [19]

Nash et al.

[11] Patent Number: 5,242,456

[45] Date of Patent: Sep. 7, 1993

[54] APPARATUS AND METHODS FOR CLAMPING TISSUE AND REFLECTING THE SAME

[75] Inventors: John Nash, Dowingtown; Kenneth Kensey, Chester Springs; Andrew R. Spriegel, Havertown, all of Pa.; Stephen Evans, Washington, D.C.

[73] Assignee: Kensey Nash Corporation, Exton, Pa.

[21] Appl. No.: 896,703

[22] Filed: Jun. 10, 1992

Related U.S. Application Data

[63] Continuation-in-part of Ser. No. 795,442, Nov. 21, 1991, abandoned.

[51] Int. Cl.⁵ .............................................. A61B 17/00
[52] U.S. Cl. ..................................... 606/142; 606/139; 606/148; 606/151
[58] Field of Search ................ 606/139, 142, 143, 151, 606/157, 158, 221, 144, 148

[56] References Cited

U.S. PATENT DOCUMENTS

| | | |
|---|---|---|
| 2,890,519 | 6/1959 | Storz, Jr. . |
| 3,579,751 | 5/1971 | Jonckheere . |
| 3,665,926 | 5/1972 | Flores .................................. 606/139 |
| 3,827,277 | 8/1974 | Weston . |
| 3,871,379 | 3/1975 | Clarke .................................. 606/148 |
| 3,877,434 | 4/1975 | Ferguson et al. .................... 606/139 |
| 3,958,576 | 5/1976 | Komiya . |
| 4,038,987 | 8/1977 | Komiya . |
| 4,177,813 | 12/1979 | Miller et al. ........................ 606/139 |
| 4,235,238 | 11/1980 | Ogiu et al. . |
| 4,274,415 | 6/1981 | Kanamoto et al. ................. 606/158 |
| 4,586,502 | 5/1986 | Bedi et al. . |
| 4,586,504 | 5/1986 | Kirsch et al. . |
| 4,671,278 | 6/1987 | Chin .................................. 606/143 |
| 4,705,040 | 11/1987 | Mueller et al. . |
| 4,741,330 | 5/1988 | Hayhurst . |
| 4,741,337 | 5/1988 | Smith et al. . |
| 4,777,949 | 10/1988 | Perlin .................................. 606/158 |
| 4,779,616 | 10/1988 | Johnson .............................. 606/148 |
| 4,796,626 | 1/1989 | De Vries ............................. 606/148 |
| 4,796,627 | 1/1989 | Tucker . |
| 4,929,240 | 5/1990 | Kirsch et al. . |
| 4,983,176 | 1/1981 | Cushman et al. . |
| 4,991,567 | 2/1991 | McCuen, II et al. . |
| 5,015,249 | 5/1991 | Nakao et al. . |
| 5,032,127 | 7/1991 | Frazee et al. . |
| 5,035,692 | 7/1991 | Lyon et al. . |
| 5,049,153 | 9/1991 | Nakao et al. . |

FOREIGN PATENT DOCUMENTS 91302837.9  3/1991  European Pat. Off. .

OTHER PUBLICATIONS

"Multipronged Laparoscopic Forceps" by H. M. Hasson appearing in The Journal of Reproductive Medicine, vol. 16, No. 4, Apr. 1976.

Primary Examiner—Stephen C. Pellegrino
Assistant Examiner—Jeffrey A. Schmidt
Attorney, Agent, or Firm—Caesar, Rivise, Bernstein, Cohen & Pokotilow, Ltd.

[57] ABSTRACT

A system and method of use for reflecting tissue located within the body of a living being. The system comprises at least one clip, a clip introducer instrument, a positioning member in the form of a tension cable assembly, and a clip removal instrument. The introducer instrument is arranged for delivering the clip through a small percutaneous incision or puncture to the situs of the tissue. The clip has a pair of jaws defining a mouth therebetween and are moveable between a open and a closed position. The jaws are biased to the closed position by an biasing member which is actuatable via the same or another percutaneous incision or puncture so that at least a portion of the tissue is trapped within the clip's mouth when it closes. The tension cable assembly comprises a flexible cable having a distal end portion and a proximal portion, and is of small diameter arranged to be extended through any percutaneous incision or puncture from outside the body of the being so that the distal end portion is coupled to the clip, with the proximal portion of the cable outside of the body of the being. The proximal portion of the cable is arranged to be moved to cause the portion of tissue trapped within the mouth of the clip to be moved to a desired position. The clip removal instrument is arranged to release the clip from the tissue and to remove it from the being's body, if desired.

81 Claims, 9 Drawing Sheets

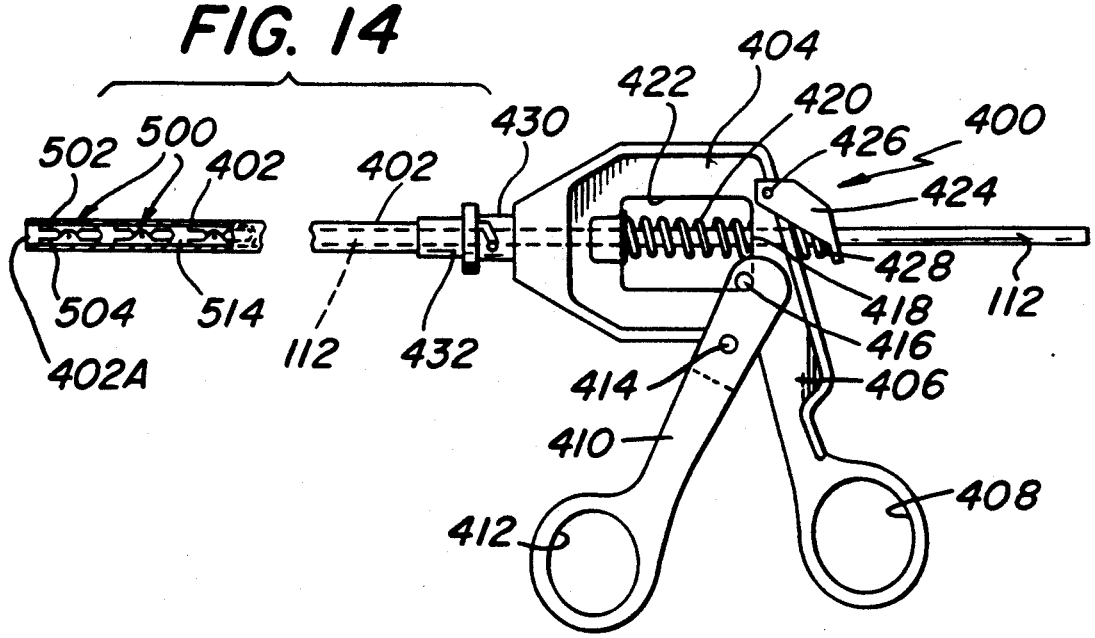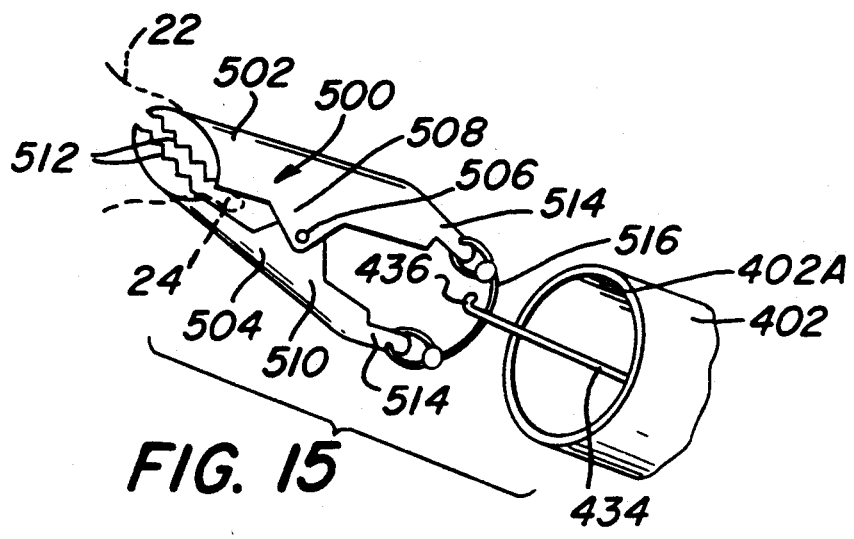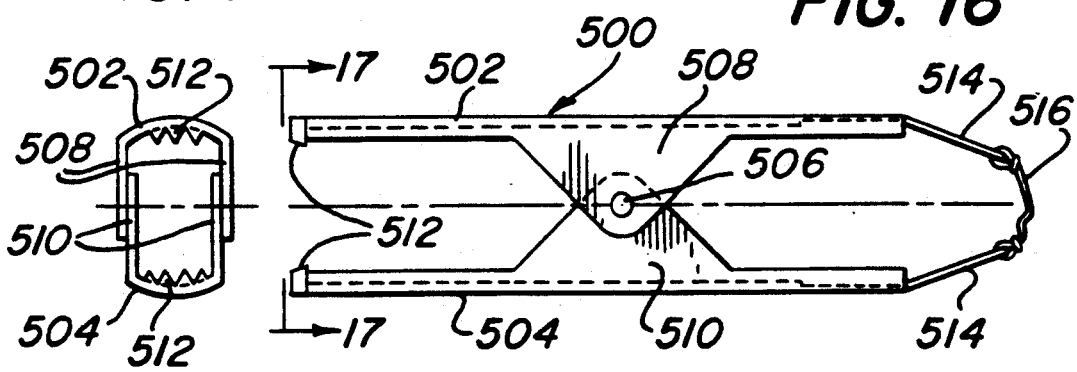

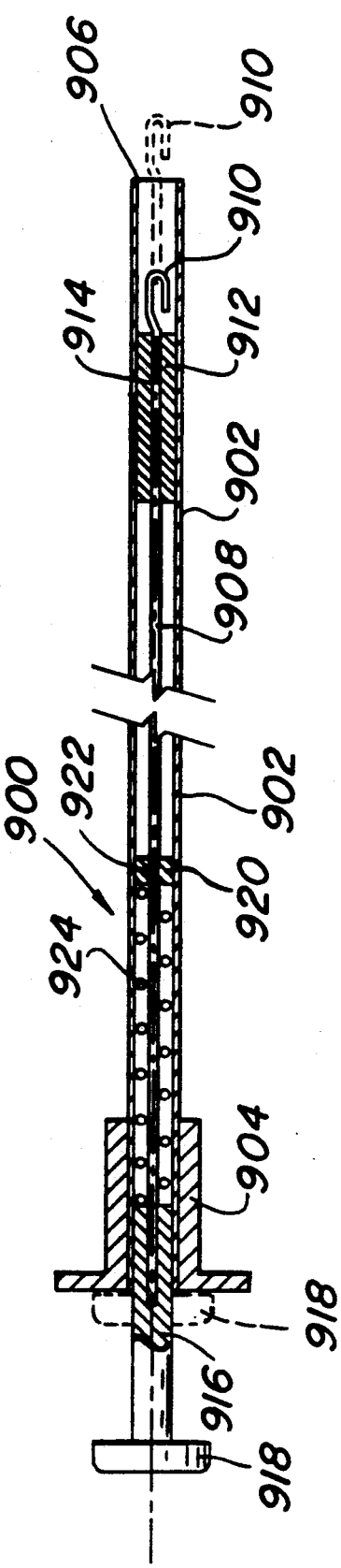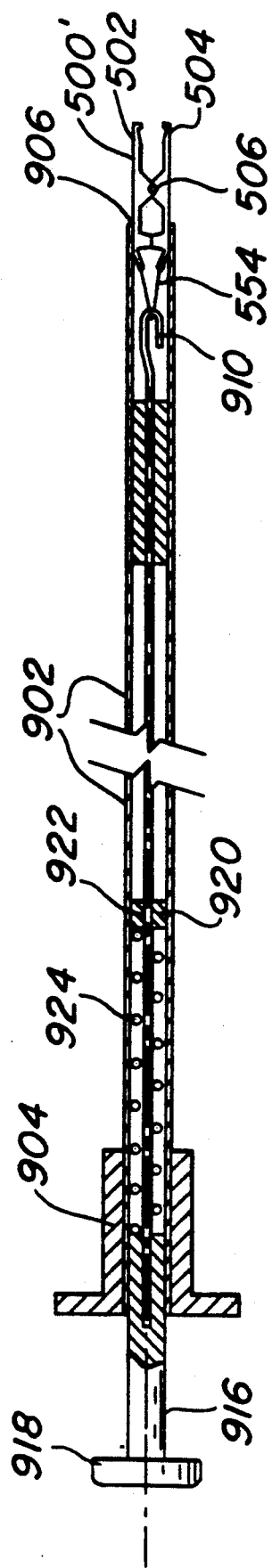

5,242,456

APPARATUS AND METHODS FOR CLAMPING TISSUE AND REFLECTING THE SAME

BACKGROUND OF THE INVENTION

This application is a continuation-in-part of application Ser. No. 07/795,442, filed on Nov. 21, 1991, now abandoned, entitled Apparatus and Methods For Dynamically Clamping Tissue, which is assigned to the same assignee as this invention and whose disclosure is incorporated by reference herein.

This invention relates generally to apparatus and methods of clamping tissue, and more particularly to apparatus and methods of clamping internal tissue during laparoscopic or other minimally-invasive medical procedures on a living being.

During surgery it is often necessary to reflect internally located tissue or organs away from a site within the body of the patient to gain access to that site and/or for better visualization. Often the surgeon will use a suture and needle for this purpose, anchoring the free end of the hemostat with a suture to some conveniently adjacent tissue, or a hemostat alone will be used. While such a procedure may be generally suitable for its intended purposes, it never the less exhibits several significant drawbacks. The most significant of those drawbacks is that the process is time consuming and not conducive to procedures in which only a small incision or puncture is made, e.g., laparoscopy, endoscopy, etc., to provide access to the interior of the patient's body. Another approach to reflecting internally located tissue entails grasping that tissue by use of some clamp-type device. The problem with that other approach is that such devices are typically quite large, and hence unsuitable for laparoscopic, endoscopic, or other small entranceway, introduction. Moreover, internally located tissue is typically quite slippery, thereby increasing the difficulty in grabbing and clamping it.

The prior art includes various tissue clamping or grasping devices designed for various purposes, e.g., to staple tissue together to effect an anastomosis. Such devices are generally not suitable for reflecting internally located tissue during laparoscopic or endoscopic procedures. Examples of such prior art devices are found in the following patents: U.S. Pat. Nos. 2,890,519 (Storz, Jr.); 3,579,751 (Jonckheere et al); 3,827,277 (Weston); 4,038,987 (Komiya); 4,586,502 (Bedi et al); 4,586,503 Kirsch et al.; 4,741,337 (Smith et al); 4,796,627 (Tucker); 4,929,240 Kirsh et al; 4,983,176 (Cushman et al); 5,015,249 (Nakao et al); 5,032,127 (Frazee et al); 5,035,692 (Lyon et al); and 5,049,153 (Nakao et al).

Various instruments are available commercially for use with conventional trocars to reflect internally located tissue. Such devices typically comprise an elongated device having a pair of grasping jaws located at the distal end of the device. The proximal end of the device typically comprises an actuating assembly, e.g., a pair of finger grips which are arranged to be squeezed together, to cause the jaws to close to grasp tissue located therebetween. Such devices, while generally effective for effecting the reflection of internally located tissue, still leave much to be desired from various standpoints. For example, each device requires the use of a conventional trocar for placement thereof. This factor substantially limits the number of devices which can be used during any operative procedure in order to keep the operating situs relatively uncluttered. Moreover, since conventional trocars typically require suturing to close the incision or puncture created thereby, it is desirable to minimize the number of trocar penetrations.

Accordingly, a need exists for some means for grasping, without penetrating or damaging, tissue located internally in the body of a living being, where access to the interior must be achieved through a very small percutaneous incision or puncture, so that the internally located tissue can be positioned as desired by use of some means extending through the same or another percutaneous incision or puncture, and without necessitating the use of a trocar.

OBJECTS OF THE INVENTION

Accordingly, it is a general object of this invention to provide apparatus and methods of use which overcome the disadvantages of the prior art.

It is a further object of this invention to provide a clip and method of use which is arranged to be inserted into the body of a living being via a very small incision or puncture to clamp a portion of internally located tissue.

It is still a further object of this invention to provide a clip and method of use which is arranged to be inserted into the body of a living being via a very small incision or puncture to clamp a portion of internally located tissue to enable the reflection of said tissue from outside the body of the being.

It is still a further object of this invention to provide a clip and instrument which is arranged to insert the clip into the body of a living being via a very small incision or puncture to clamp a portion of internally located tissue without penetrating or damaging that tissue.

It is yet a further object of this invention to provide an instrument which is arranged to be inserted into the body of a living being via a very small incision or puncture to retrieve a clip clamped to a portion of internally located tissue.

It is yet a further object of this invention to provide a method for reflecting, positioning, and/or holding in position internally located tissue through a small incision or puncture.

SUMMARY OF THE INVENTION

These and other objects of this invention are achieved by providing a system and method of use for reflecting tissue located within the body of a living being.

The system comprises at least one clip, an introducer instrument, and an elongated positioning member. The introducer instrument is of a small diameter arranged for delivering the clip through a small percutaneous incision or puncture to the situs of the tissue. The clip comprising a pair of jaws and a biasing member. The jaws have portions defining a mouth therebetween and are moveable between a first orientation, wherein they are disposed apart, and a second orientation, wherein they are disposed closer together The biasing member is coupled to the jaws and is actuatable via the same or another percutaneous incision or puncture to move them from the first orientation to the second orientation so that at least a portion of the tissue is trapped within the clip's mouth.

The elongated positioning member has a distal end portion and a proximal portion, and is of small diameter arranged to be extended through any of the percutaneous incisions or punctures from outside the body of the being so that the distal end portion is coupled to the clip, with the proximal portion of the elongated positioning member being located outside of the body of the being. The proximal portion is arranged to be moved to cause the portion of tissue trapped within the mouth of the clip to be moved to a desired position.

The method of this invention entails inserting the clip through a first incision or puncture, locating portions of the clip's jaws immediately adjacent the tissue to be reflected, and then actuating the biasing means to cause the jaws to move to the second orientation so that a portion of the tissue is trapped within the clip's mouth.

The elongated positioning element is extended through the first incision or puncture or a second percutaneous incision or puncture so that it is coupled to the clip. Then the elongated positioning element is manipulated from outside of the body of the being to effect the reflection of the tissue.

In some embodiments of the invention the elongated positioning element comprises a tether which is connected to the clip as introduced. The tether is arranged to be pulled to effect the movement or positioning of tissue to which the clip is secured. Plural clips may be coupled to each other via at least one tether in a pulley arrangement to effect the movement or positioning of tissue to which one or more of the clips is clamped. In other embodiments of the invention the positioning means additionally comprises a hammock-like assembly coupled between a pair of clips for holding a portion of internal tissue thereunder.

BRIEF DESCRIPTION OF THE DRAWING

Other objects and many of the attendant advantages of this invention will be readily appreciated as the same becomes better understood by reference to the following detailed description when considered in connection with the accompanying drawings wherein:

FIG. 14 is a side elevational view, partially in section, of the entire tool shown in FIG. 11;

FIG. 15 is an isometric view showing another alternative embodiment of a clip constructed in accordance with this invention used with a tool like that shown in FIGS. 11-14;

FIG. 16 is an enlarged side elevational view of the clip shown in FIG. 15;

FIG. 17 is an end view of clip taken along line 17—17 of FIG. 16;

FIG. 23 is a plan view, partially in section, showing a clip removal tool constructed in accordance with this invention for effecting the removal of clips constructed in accordance with this invention from the body of the being; and FIG. 24 is a view of the removal tool of FIG. 23 showing the removal of a clip from the body of the being.

DETAILED DESCRIPTION OF THE PREFERRED EMBODIMENT

Figure 1:
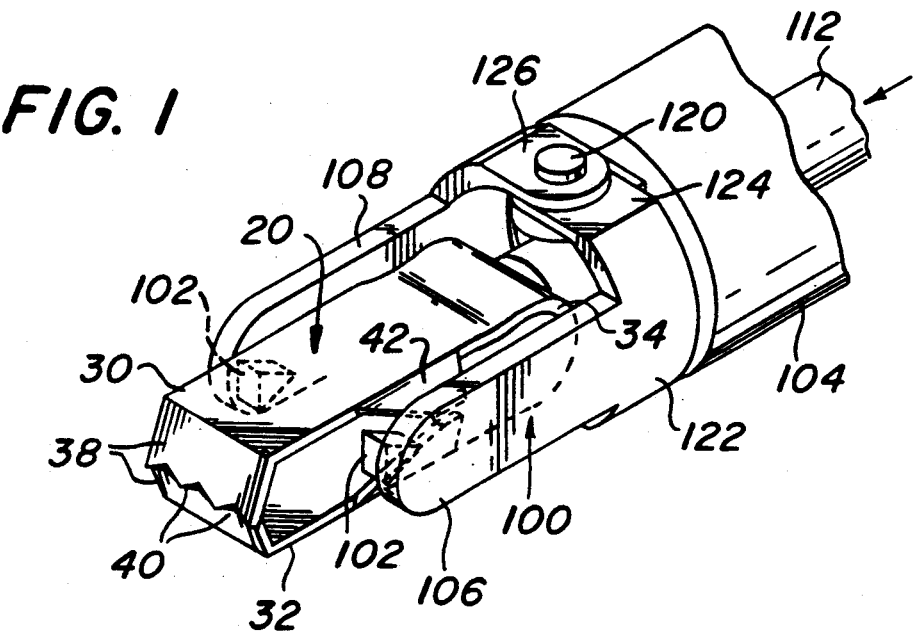
FIG. 1 is a isometric view of a clip and the distal end of an instrument or tool for applying it, both of which are constructed in accordance with this invention, and shown prior to the securement of the clip to internally located tissue within the body of a living being.
Figure 20:
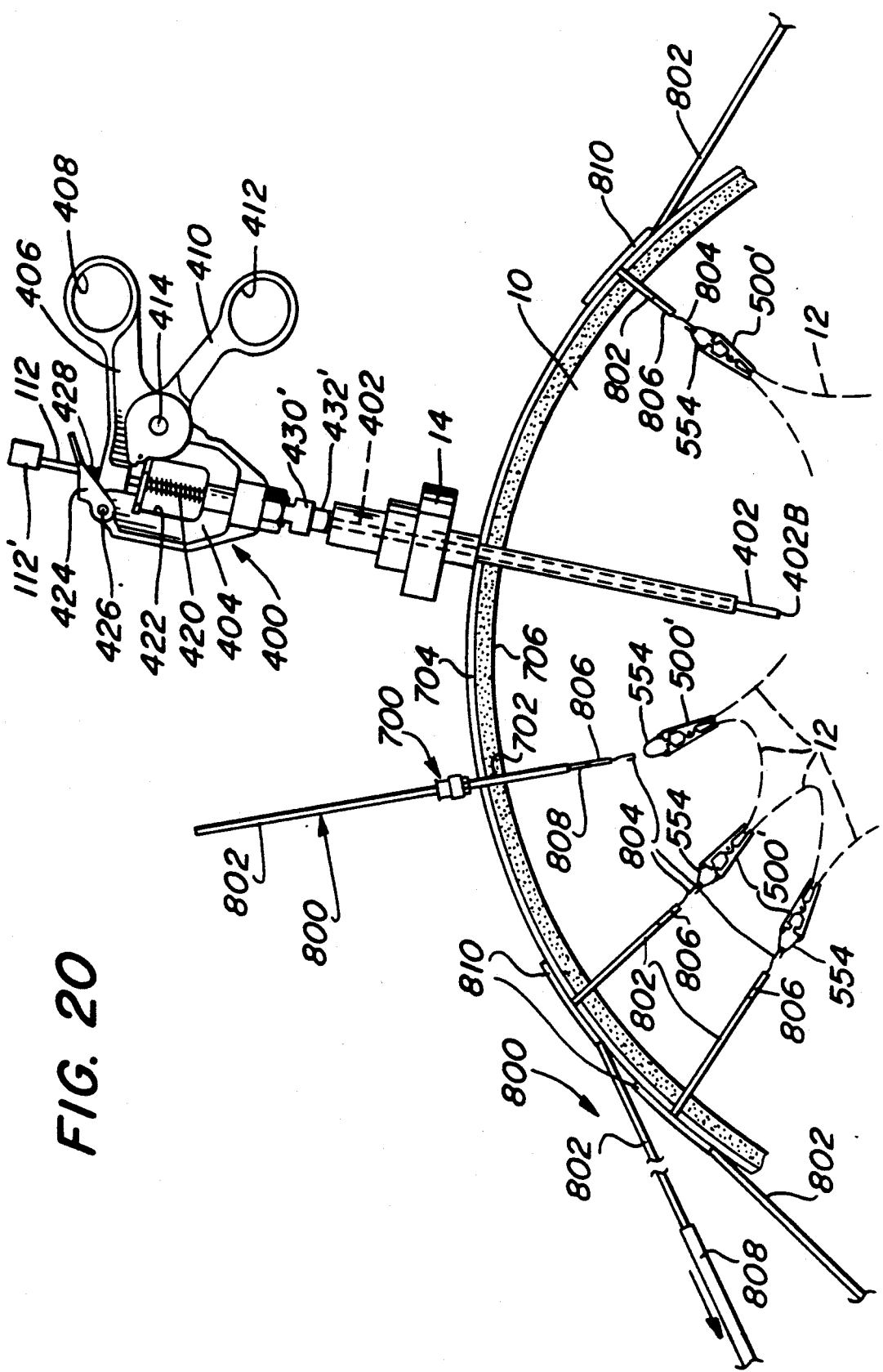
FIG. 20 is a side elevational view, partially in section, of the abdomen of a living being shown with interior portions thereof being reflected by a system constructed in accordance with this invention.

Referring now in greater detail to the figures there is shown at 100 in FIG. 1, at 400 in FIGS. 11-14, and at 400' in FIG. 20 an instrument or tool forming part of a system for introducing one or more clips 100 and 100' through a small percutaneous incision or puncture (not shown) in the body of a patient to attach the clip(s) to some internal organ or tissue 22 (FIGS. 2, 4-6, 9-13, 15, and 20), so that the clip(s) can be coupled to some positioning means extending through that percutaneous incision or puncture or some other percutaneous incision or puncture, whereupon the tissue to which the clip(s) is(are) attached can be reflected, moved or otherwise brought to some desired location, by manipulating the positioning means from outside the body of the patient.

Figure 9:
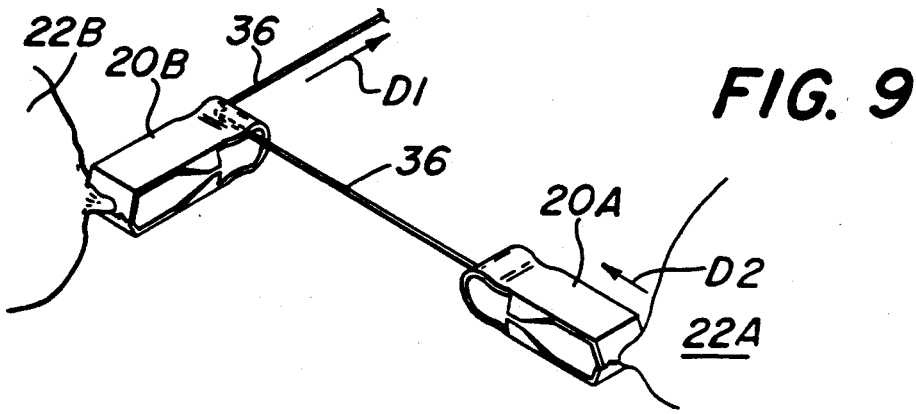
FIG. 9 is a isometric view of two clips constructed in accordance with one aspect of this invention secured to respective portions of internally located tissue in accordance with one aspect of the method of this invention.
Figure 10:
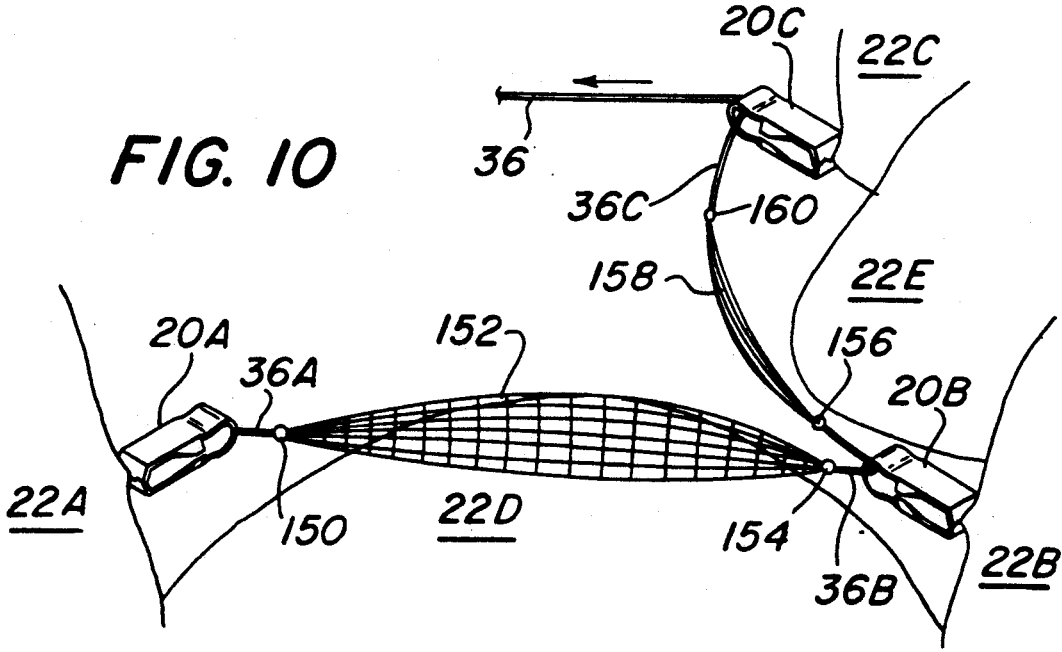
FIG. 10 is a isometric view of three clips constructed in accordance with another aspect of this invention secured to respective portions of internally located tissue in accordance with another aspect of the method of this invention.
Figure 11:
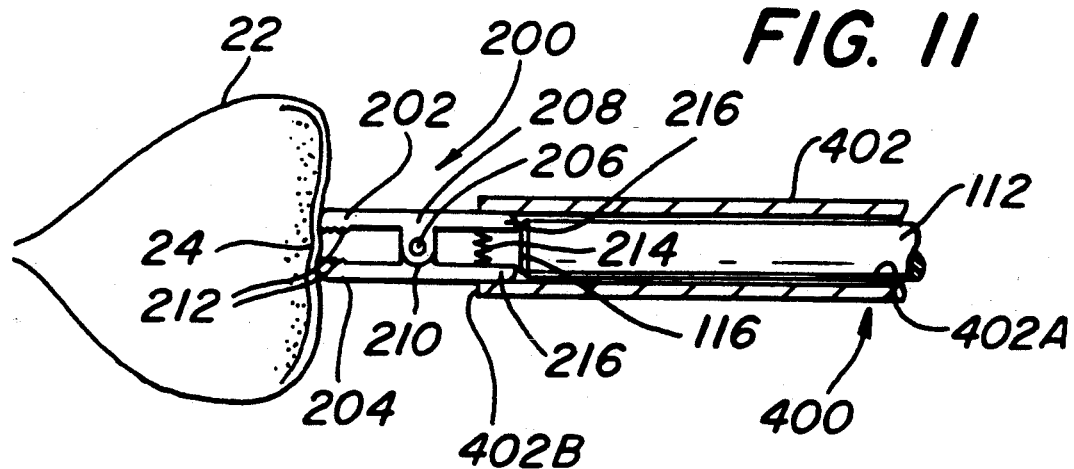
FIG. 11 is a side elevational view, partially in section, of another embodiment of a clip and another embodiment of a tool for applying it constructed in accordance with this invention and shown at an initial point during the securement of the clip to internally located tissue.
Figure 12:
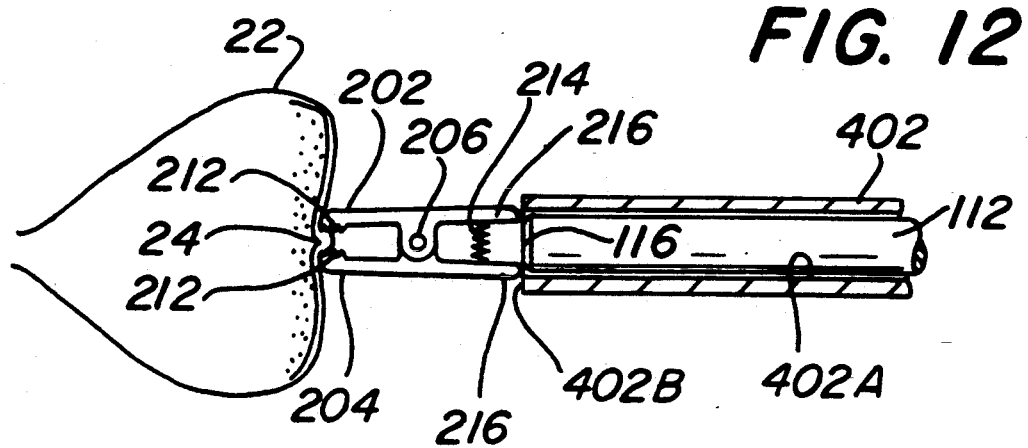
FIG. 12 is a side elevational view, partially in section, of the clip and the tool shown in FIG. 11 after the securement of the clip to internally located tissue, but prior to removal of the tool.
Figure 13:
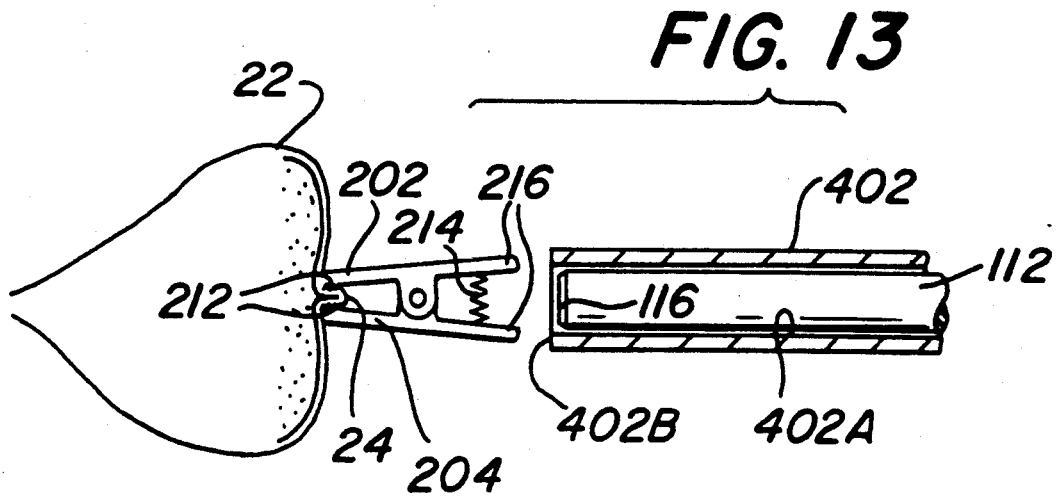
FIG. 13 is a side elevational view, partially in section, of the clip shown in FIG. 11 after its securement to the internally located tissue and after the tool has been removed.

Four exemplary embodiments of clips constructed in accordance with this invention are shown and described herein. In particular one embodiment of the clip is shown in FIGS. 1-10 and is denoted by the reference numeral 20. Another embodiment of the clip is shown in FIGS. 11-13 and is denoted by the reference numeral 200. Yet another embodiment of the clip is shown in FIGS. 15-17 and is denoted by the reference numeral 500. Lastly, another embodiment of the clip is shown in FIGS. 18, 19, 20, 21, and 24. That embodiment of the clip is a slight modification of clip 500 and is denoted by the reference numeral 500'.

As will be described in detail later the clips 20, 200, and 500, each include a positioning/holding means in the form of a flexible filament or tether connected to it when inserted into the body of the being through a percutaneous incision or puncture to enable the surgeon to pull on the tether to move, e.g., reflect, the tissue 22 to which the clip is secured to some desired position, e.g., out of the way of the surgeon's line of sight through the incision or puncture. As will also be described later either of the clips 20, 200, and 500 may be coupled to one or more similarly constructed clips located within the body of the patient at a different location to form a pulley-like arrangement for expediting the tissue moving and/or positioning procedure. Moreover, the positioning/holding means may additionally comprise a web-like material (also to be described later) arranged to be coupled to another internally located clip to form a hammock-like barrier or retainer holding a portion of internally located tissue in position, e.g., out of the way of the operative site.

Figure 19:
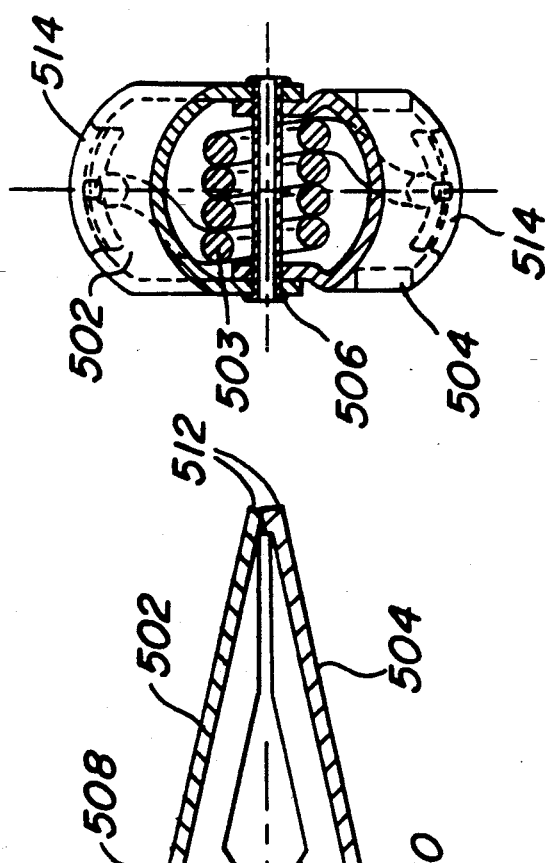
FIG. 19 is a sectional view of clip of FIG. 18 taken along line 19—19.
Figure 18:
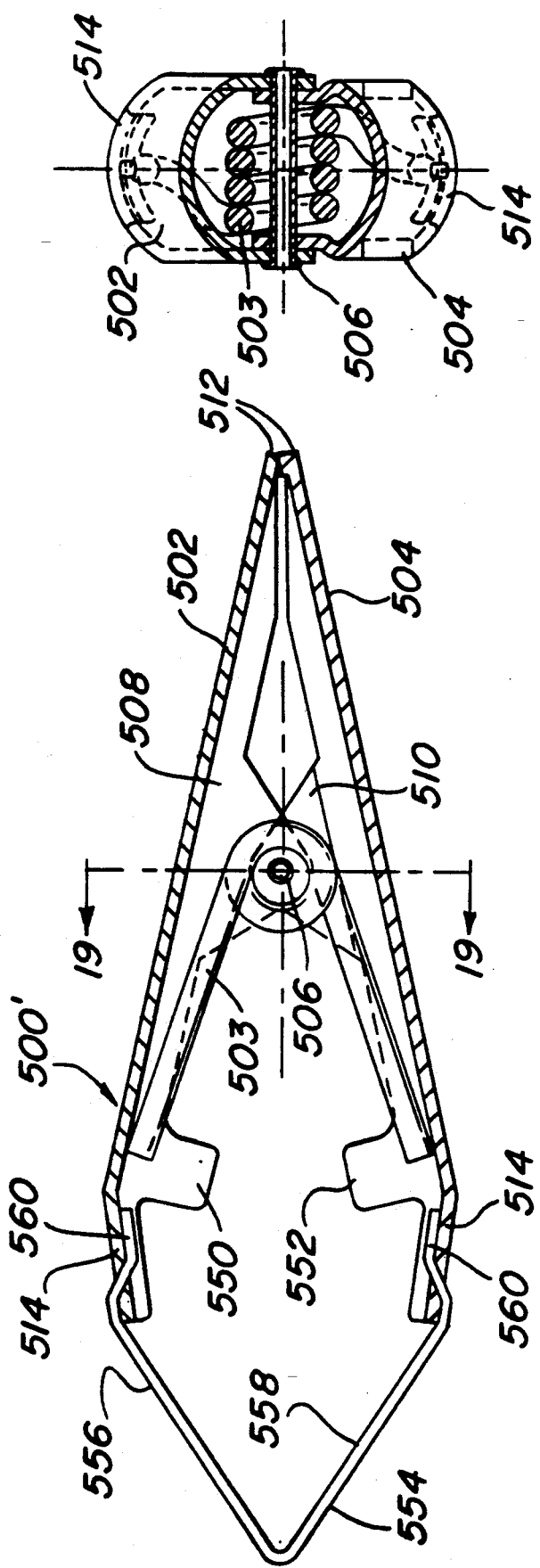
FIG. 18 is a side view showing another alternative embodiment of a clip constructed in accordance with this invention used, and which is basically constructed like the clip of FIG. 15, and which is arranged to be used with a tool like that shown in FIGS. 11-14 or with a tool like that shown in FIG. 20 which is also constructed in accordance with this invention.

In the embodiment of FIGS. 18 and 19 the clips 500' do not include any positioning/holding means connected to them (as is the case of clips 500) when they are inserted into the body of the being. Instead each clip 500' is constructed and arranged to be coupled to separate positioning/holding means which extends through any suitable percutaneous incision or puncture after the clip has be located in position within the body of the being and secured to the tissue to be reflected. The structure and operation of the clips 500' and of the system for introducing and positioning them will be described later with reference to FIG. 20.

Figure 2:
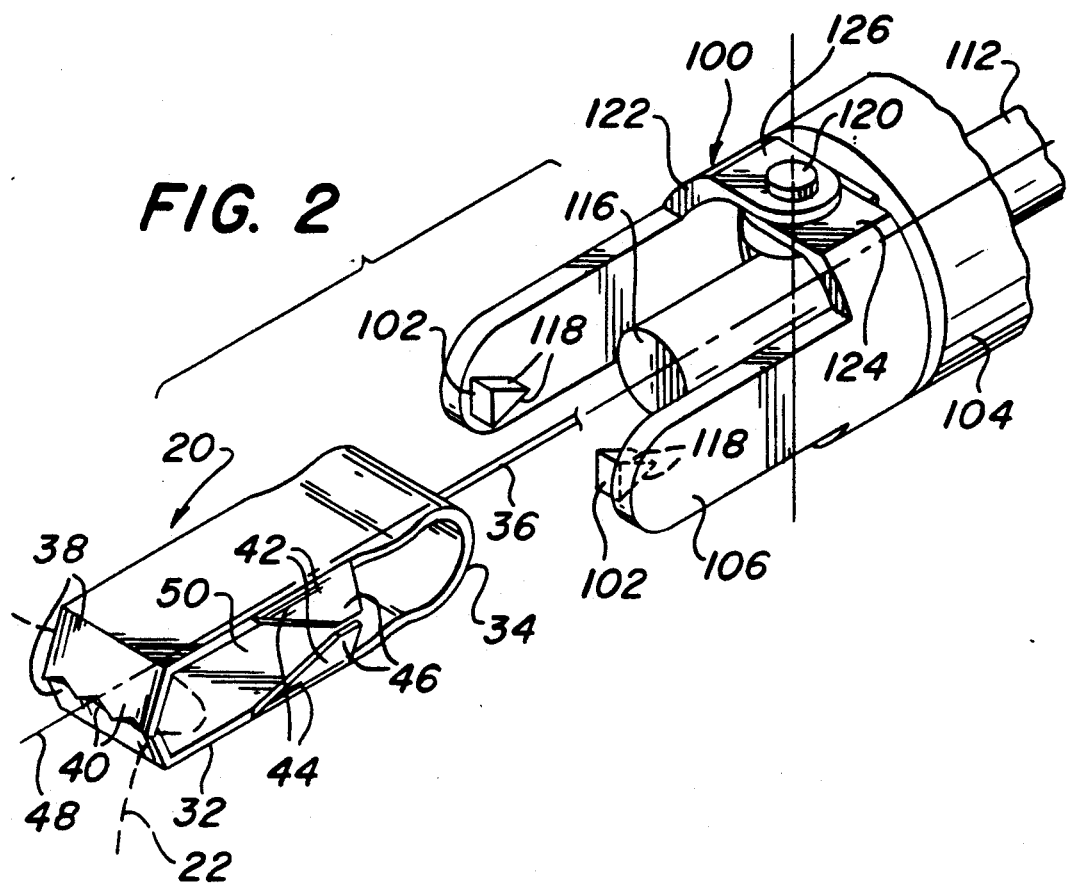
FIG. 2 is a isometric view of a clip and the distal end of the tool of FIG. 1 shown after to the securement of the clip to such internally located tissue.

As can be seen clearly in FIGS. 1 and 2 the clip 20 basically comprises a pair of jaws 30 and 32, connected by bridging section 34, and a holding member 36. In this embodiment the holding member comprises a filament or tether, connected to the bridging section. Each of the jaws 30 and 32 terminates in an angularly extending a free end 38, whose distal edge 40 is serrated. The serrated edges 40 define what may be called the "mouth" of the clip between the free ends of the jaws 30 and 32.

The bridging section 34 of the clip 20 is a generally U-shaped member which cooperates with the jaws 30 and 32 to serve as a biasing means to bias the jaws into a closed orientation, wherein their free end edges 40 engage each other to thereby "close" the clip's "mouth". In this regard, and in accordance a preferred embodiment of this invention, the clip 20 is formed as an integral unit of a resilient material, e.g., stainless steel, so as to form a spring frame wherein the innate resiliency of the frame, and particularly its bridging section 34, naturally biases the jaw closed.

As will be described later the jaws 30 and 32 also include cam means thereon which are arranged to cooperate with other cam means forming a portion of the tool 100 to open the clip's mouth like that shown in FIG. 3 in order to enable the clip to clamp or grasp onto the tissue portion 22.

In accordance with a preferred embodiment of this invention the clip 20 of FIG. 1, the clip 200 or FIG. 11, and the clip 500 of FIG. 15 are each quite small, e.g., 0.180 inch (4.57 mm) in diameter by 0.7 inch (17.8 mm) long so that they can be applied using a tool which can fit through a 5 mm sheath or introducer for use in laparoscopic or endoscopic surgery. It must, however, be pointed out that the clips 22 and 200 of this invention can be of different dimensions, e.g., larger, for various types of applications, e.g., manual securement.

Irrespective of the size or shape of the clips, each is constructed and arranged to be oriented so its mouth is open by the time it is adjacent the tissue to be grasped and its biasing means actuated to cause the clip to snap closed to grab or grasp the tissue without penetrating it. As should be appreciated by those skilled in the art, internally located tissue, particularly soft, lightly pressurized tissue, e.g., a blood vessel, the gall-bladder, the urinary bladder, the colon, a hernia, an aneurysm, etc., is typically quite slippery and difficult to grasp. To overcome that problem, the clips of this invention are designed to snap closed virtually instantaneously upon their "release" (as will be described in detail later). Such closing action produces a tissue wave at the edge of the jaws. That wave gets trapped between the jaws, i.e., within the mouth of the clip, to result in a firm, reliable, yet non-penetrating, grasp on the tissue. Thus, each of the clips of the subject invention can be said to "dynamically" clamp or trap wet or slippery tissue without the tissue slipping or popping away from or out of the clip's mouth.

Figure 3:
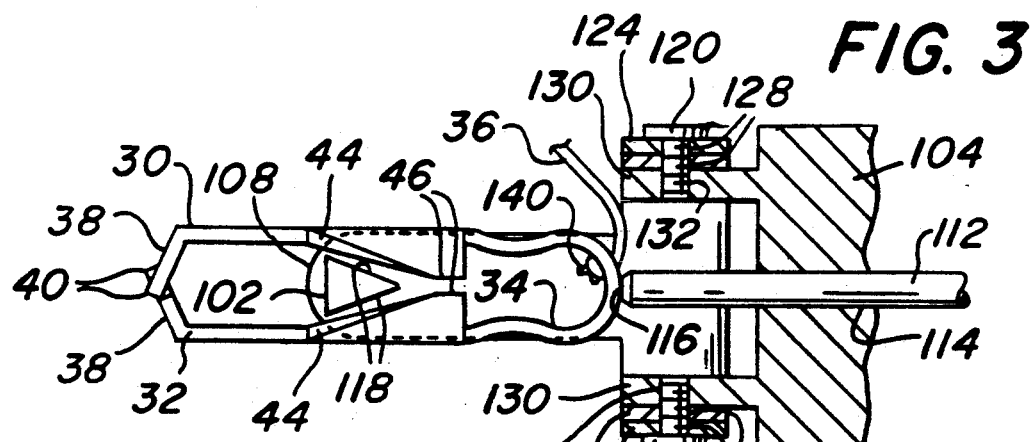
FIG. 3 is a side elevational view, partially in section, of the clip and the tool shown in FIG. 1 prior to the securement of the clip to internally located tissue.

Attention is now directed to FIGS. 1 and 3 for a description of the cam means referred to earlier for effecting the opening the clip's mouth. Thus, as can be seen therein each of the jaws 30 and 32 includes a pair of ramps 42. One of the ramps 42 of one pair projects outward and downward from one marginal edge of the upper jaw 30, while the other ramp 42 of that pair projects outward and downward from the other marginal edge of that jaw. In a similar manner one ramp 42 of the other pair projects outward and upward from one marginal edge of the lower jaw 32, while the other ramp 42 of that pair projects outward and upward from the other marginal edge of that jaw. Each ramp 42 includes an inclined cam surface 44 terminating in a "release" surface 46. The release surface extends parallel to the central longitudinal axis 48 of the clip and the applicator tool 100. Thus, the cam surfaces on the marginal edge of one side of the jaw 30 oppose the cam surfaces on the corresponding marginal edge of the jaw 32 to form a Y-shaped slot 50. The cam surfaces on the marginal edge of the other side of the jaw 30 are arranged in an identical manner.

The cam surfaces of each of the Y-shaped slot 50 are arranged to be engaged by respective wedge-shaped cam members or trunnions 102 forming a portion of the tool 100 to open the jaws of the clip. This action occurs as the clip 20 is ejected from the tool 100. Before describing the ejection procedure a description of the tool 100 is in order.

Figure 4:
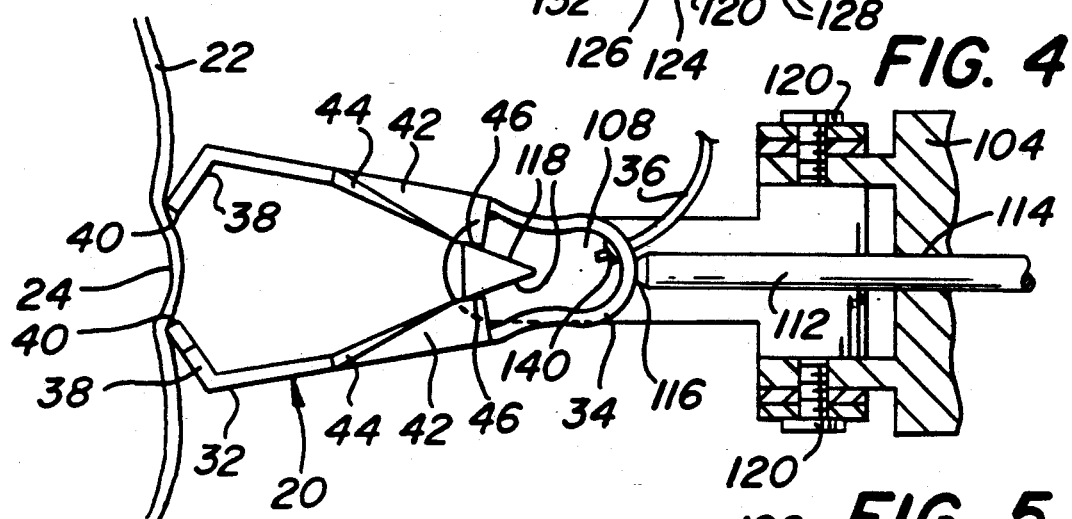
FIG. 4 is a side elevational view, partially in section, of the clip and the tool shown in FIG. 3 during the securement of the clip to internally located tissue.
Figure 5:
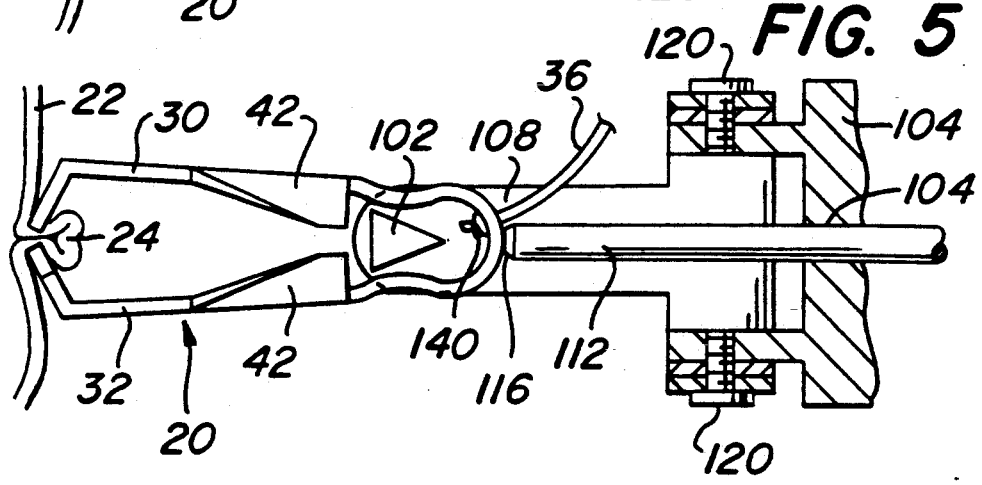
FIG. 5 is a side elevational view, partially in section, of the clip and the tool shown in FIG. 3 after the securement of the clip to internally located tissue, but prior to removal of the tool.
Figure 6:
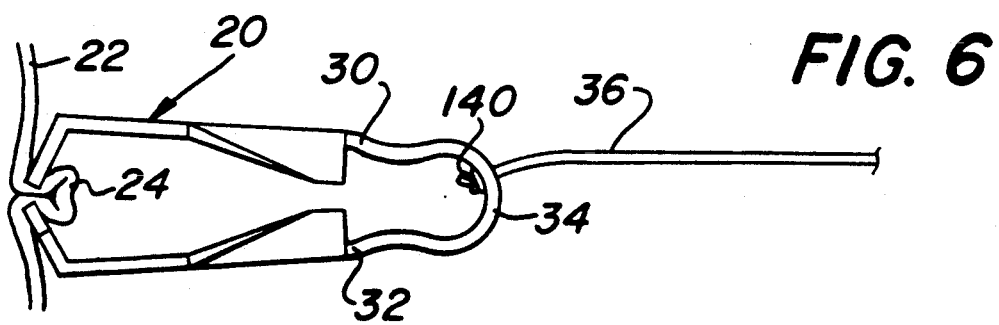
FIG. 6 is a side elevational view, partially in section, of the clip shown in FIGS. 1 and 3 after its securement to the internally located tissue, but after the tool has been removed.

Thus as can be seen in FIGS. 2 and 3 the tool 100 includes a body portion 104 having a pair of swing jaws 106 and 108 mounted at the distal end of the body. The jaws 106 and 108 basically comprises a pair of elongated members which extend generally parallel to the longitudinal axis 48. They are mounted to pivot or swing outward about a transverse axis 110 extending perpendicular to the tool's central longitudinal axis 48 by means to be described later. The clip 20 is arranged to be located in the space between the swing jaws 106 and 108 as shown in FIGS. 1 and 3. A pusher member 112, in the form of an elongated rod, extends down a central passageway 114 (FIG. 3) in the tool's body 104 so that its distal end 116 is immediately adjacent (or even abutting) the bridging section 34 of the clip 20. The pusher member is arranged to be operated by means (not shown) at the proximal end of the tool to slide it in the distal direction down the passageway 114 to thereby push the clip 20 longitudinally out from the space between the swing jaws 106 and 108 as shown in FIGS. 4 and 5.

Each of the wedge-shaped trunnions 102 includes a pair of cam surfaces 118 which are inclined with respect to each other and merge together. Each trunnion 102 is projects from the inner surface of a respective one of the swing jaws 106 and 108 immediately adjacent the distal end thereof and is located within a respective Y-shaped slot 50 in the clip 20 (see FIG. 3).

The cam surfaces 118 of each trunnion 102 are oriented so that they merge together in the proximal direction. These surfaces are arranged to engage the inclined cam surfaces 42 of the clip as the clip is ejected by the pusher member 112 to pry the jaws 30 and 32 apart in opposition to the bias force produced by the bridging section 36. In particular, as the pusher member 112 pushes the clip longitudinally down the axis 48 the cam surfaces 118 on the trunnions 102 engage respective cam surfaces 44 on the ramps 42. Continued movement of the clip in the proximal direction causes the cam surfaces 118 to ride along the cam surfaces 44, and from there they move onto the release surfaces, thereby progressively opening the clip's jaws 30 and 32 until the mouth of the clip is fully open. This occurs when the cam surfaces 118 reach the proximal ends of the release surfaces 46. As soon as the cam surfaces 118 pass the proximal ends of the release surfaces 46, the jaws 30 and 32 immediately snap together as a result of the bias of the bridging section 34, thereby instantly closing the clip's mouth.

The swing jaws 106 and 108 are mounted to pivot about the axis 110 via a pair of threaded members, e.g., screws, 120. In particular each swing jaw includes an arcuate proximal portion 122 of the same outer cylindrical profile and diameter as the body 104 of the tool 100. The proximal portion 122 of the swing jaw 106 in turn includes a pair of diametrically opposed flatted end sections 124. In a similar manner the proximal portion 122 of the swing jaw 108 includes a pair of diametrically opposed flatted end sections 126. Each flatted end section includes a hole 128 therein. The pair of flatted end sections 124 of the swing jaw 106 are disposed between the pair of flatted end sections 126 of the swing jaw 108 and with their holes 128 axially aligned.

The body 104 of the tool 100 includes a pair of brackets 130 projecting longitudinally outward from the proximal end thereof. Each bracket 130 includes a threaded hole 132 therein. The holes 132 in the brackets are aligned with the holes 128 in the swing jaws 106 and 108. Each of the screws 120 is extended through a pair of aligned holes 128 in the swing jaws and is threadedly engaged into the aligned hole 13 in the bracket to pivotally mount the swing jaws thereon.

The operation of the tool 100 to secure a clip 20 onto a portion of tissue located within the body of a patient will now be described. The tool 100 with the clip 20 located therein is introduced through a small percutaneous incision or puncture (not shown) within the body of the patient using any suitable conventional tubular sheath (not shown) extending through that puncture or incision until the distal end of the tool is located at the site of the tissue to be grasped. The pusher member 112 is then operated as described above to start to eject the clip 20 from the tool and at the same time commence opening the clip's mouth. In particular the tool is positioned so that it engages the tissue 22 to be grasped when the clip's mouth is fully open so that a portion 24 of that tissue 22 extends slightly into the open mouth as shown in FIG. 4. Continued operation of the pusher 112 causes the cam surfaces 118 of the trunnions 102 to clear the release surfaces of the clip's ramps 42 (as described earlier), whereupon the jaws immediately snap closed, thereby trapping the portion 24 of the tissue between the serrated free ends of the clip's mouth as shown in FIG. 3.

The tool 100 then is preferably retracted slightly to enable the surgeon to test if the clip has, in fact, grasped the tissue. In this regard, since the trunnions 102 will still be located between the clip's jaws, a slight retraction of the tool will cause the proximal end of each trunnion 102 to engage the inner surface of the bridging section of the clip if the clip has secured itself to the tissue 24, whereupon the surgeon will notice a slight resistance to continued retraction of the tool.

In accordance with a preferred aspect of this invention the clips are precisely constructed so that the amount of clamping force their jaws apply to the tissue trapped therebetween is controlled and sufficiently low so that penetration of the tissue does not result.

Once the surgeon has determined that the clip 20 has successfully grasped the tissue 22, such as shown in FIG. 3, the swing jaws 106 and 108 are operated by means (not shown) to cause them to swing outward from the longitudinal axis 48 of the tool. This action frees the clip from the tool by removing the trunnions 102 from between the rear of the clip's jaws 30 and 32. The tool 100 is then retracted further until the swing jaws can be pivoted back to the orientation shown in FIGS. 2, yet still clear the clip. Once this has been accomplished the tool can be removed from the sheath extending into the puncture by retracting it fully from the sheath.

At this time the surgeon is ready to reflect the tissue 22 to a desired position within the patients body, e.g., to provide a line of site to another internal portion which was blocked by the presence of the tissue portion 22. This action is achieved by use of the holding filament or tether 36. In accordance with a preferred embodiment of this invention the tether is formed of any suitable flexible member, e.g., a 2.0 monofilament. The distal end of the tether extends through a hole (not shown) in the clip's bridging section 34 and located on axis 48. The tether is secured in place by a knot 140.

The proximal end of the tether extends from the clip 22 through the sheath to the outside of the patient's body. Thus, all that is necessary for the surgeon to do to effect the desired positioning of the grasped tissue is to pull on the exteriorly located portion of the tether until the desired positioning is accomplished. The laprascopic or endoscopic procedure can then be carried out, with the reflected tissue now being out of the way to give the surgeon a good line of sight and to free space within the body at the operative site at which he/she can work.

The tool 100 is also arranged to effect the removal of the clip 20 from within the body of the patient after its use is no longer required or desirable. Like the insertion action the removal action can also be accomplished through the small percutaneous incision or puncture. In this regard when it is desired to remove the clip 20 the tool 100 is reintroduced into the body of the patient through the puncture until the distal ends of the swing jaws 106 and 108 are adjacent the clip. The swing jaws are then pivoted open by the same means which had been operated during the clip securement procedure and the tool positioned so that its swing jaws can be pivoted back to the closed orientation (like that shown in FIG. 1) but with the trunnions of the swing jaws located within the Y-shaped slots 50 in the clip. Once the swing jaws are pivoted back to the orientation such that the trunnions 102 are within the Y-shaped slots the tool is then retracted. This action causes the cam surfaces 118 of the trunnions to ride up the cam surfaces 44 of the clip to thereby open the clip's jaws and release the tissue 24. Once the cam surfaces 118 of the trunnions clear the release surfaces 46 of the clip, the clip will again snap shut, but the trunnions will remain in the space bounded by the clip's bridging section 34. Accordingly, further retraction of the tool through the puncture will cause those trunnions to engage the inner surface of the bridging section to also retract the now-freed clip 20. The tool and clip are then retracted as a unit until they are outside the body of the patient.

In accordance with one preferred aspect of this invention two or more of any of the clips 20, 200, and 500 can be introduced into the body of the patient at different locations and the clips can be coupled together to form a pulley-like configuration to expedite the tissue reflection procedure. One example of such action is shown in FIG. 9 where it can be seen that one clip 20A constructed in accordance with this invention has been placed so that it has grasped one portion 22A of internal tissue. The tether 36 of this clip is extended through the space between the jaws 30 and 32 and the bridging section 34 of a second clip 20B. The second clip 20B has been positioned and operated so that it has grasped another portion 22B of internal tissue. The proximal end of the tether 36 extends through any suitably located percutaneous incision or puncture (not shown) to a point outside the body of the patient. Accordingly, when the surgeon pulls on the tether in the direction of the arrow D1, the direction of the pulling force on the clip 20A (and hence the tissue grasped by it) will be changed by the passage of the tether 36 through the clip 20B to the direction shown by the arrow D2. Thus, by appropriate placement of one or more clips 20 the surgeon may position tissue at any desired location irrespective of the direction of the pulling force applied to the tether through the puncture or incision.

It should be pointed out at this juncture that each clip may have its own tether for coupling to one or more other clips, depending upon the configuration desired.

In accordance with another preferred aspect of this invention two or more of any of the clips 20, 200, and 500 can be introduced into the body of the patient at different locations and the clips can be coupled together to form a system including one or more hammock-like, tissue retainers to expedite a tissue reflection/retaining procedure. One example of such action is shown in FIG. 10 where it can be seen that one clip 20A constructed in accordance with this invention has been placed so that it has grasped one portion 22A of internal tissue. A second, similar, clip 20B has been placed so that it has grasped a second portion 22B of internal tissue. A third, similar, clip 20C has been placed so that it has grasped a third portion 22C of internal tissue. A section 36A of the tether 36 of the clip 22A is secured to one end 150 of a hammock-forming web 152. The other end 154 of the web 152 is connected to a second section 36B of the tether 36 and is extended through the space between the jaws 30 and 32 and the bridging section 34 of the second clip 22B. The extending tether section 36B is in turn connected to one end 156 of a second, hammock-forming web 158. The other end 160 of the web 158 is connected to a third section 36C of the tether 36. The tether section 36C is extended through the space between the jaws 30 and 32 and the bridging section 34 of the third clip 22C and from there through a percutaneous incision or puncture (not shown) to a point outside the body of the patient.

Each of the hammock-like retainer members 152 and 158 is arranged to be spread out to form a barrier wall for holding or retaining a portion of internal tissue behind it. In the interests of expediting the insertion of the retaining system shown in FIG. 10 into the body of the patient by percutaneous incision the hammock-like retainer members are each formed of a woven or mesh-like material. This enables them to be compressed down to a very small external cross sectional area. Once inserted into the body of the patient the retainer members can be spread out. Thus, for example, retainer member 152 can be spread out by the surgeon to the orientation shown in FIG. 10 to hold back a portion 22D of tissue located between portions 22A and 22B. In a similar manner retainer member 158 can be spread out by the surgeon from the compacted orientation shown in FIG. 10 to hold back a portion 22E of tissue located adjacent to it. Moreover, since the clips and retainer members are all coupled together the pulling on the exteriorly located tether can enable the surgeon to position the grasped and retained tissue as desired.

It should be pointed out at this juncture that other hammock-like systems can be provided to accomplish tissue reflection or retention. Thus, for example a hammock-like member formed of a triangular mesh may be spread out and held in place within the body of the patient to retain tissue behind it by use of three clips 20, with each clip securing a respective corner of the member to the tissue. Thus, the system shown in FIG. 10 is merely exemplary.

Figure 7:
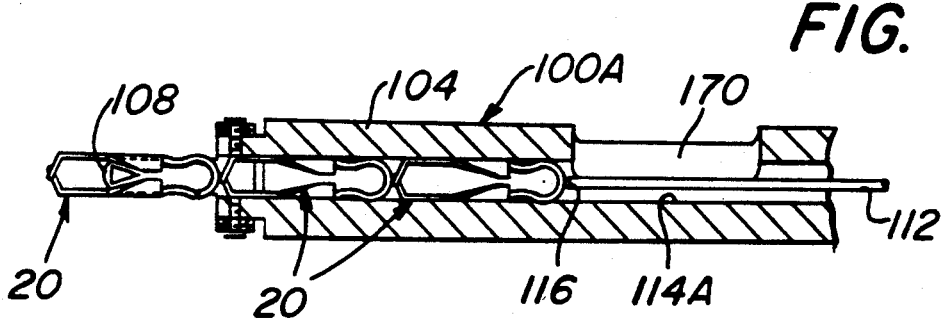
FIG. 7 is a side elevational view, partially in section, of an alternative embodiment of the tool shown in FIGS. 1-5.

In FIG. 7 there is shown an alternative embodiment of the tool 100A constructed in accordance with this invention to enable the loading of a stack or column of clips 20 therein. The embodiment of the tool 100A shown in FIG. 7 is identical to that of tool 100 shown in FIG. 1 except for the clip loading mechanism (as will be described hereinafter). Thus, in the interest of brevity only that portion of the tool 100A will be described.

As can be seen in FIG. 7 the body portion 102 of the tool 100A includes a breech port 170 communicating with passageway 114A. The passageway 114A is similar to passageway 114 of tool 100 except that it is of a larger internal diameter to accommodate a stack of breech loaded clips 20 therein.

The distal end of the passageway 114A opens to the space between the swing jaws 106 and 108 to deposit the distal-most clip 20 of the stack of clips into that space. The pusher member 112 is located in the passageway 114A and can be moved to a longitudinal position therein so that its distal end 116 is located proximally of the breech port 170. Accordingly, in order to load a stack of clips within the tool 100A all that is necessary is to retract the pusher member to that position and then to sequentially feed clips 20 into the port, sequentially using the pusher to position them in a stack or column until the distal-most clip 20 is located in the space between the swing jaws. Each of the clips 20 includes a tether like that described heretofore. Such tethers are not shown in FIG. 7 in the interest of drawing simplicity.

The tool 100A is used in a similar manner as that described heretofore, with the most distally located clip being pushed out of the tool by the next successive clip under the force applied by the pusher member.

Figure 8:
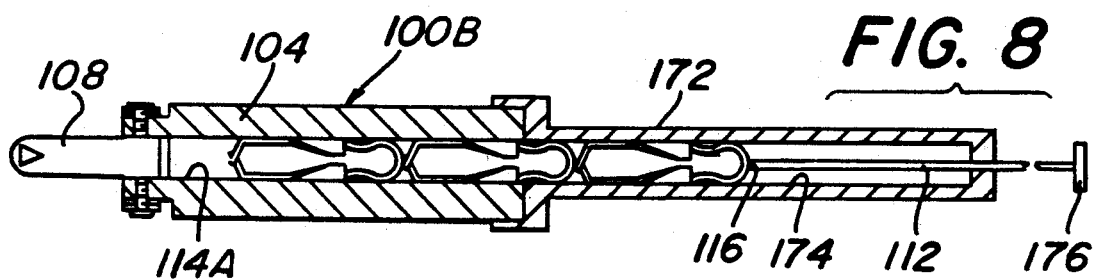
FIG. 8 is a side elevational view, partially in section, of another alternative embodiment of the tool shown in FIGS. 1-5.

In FIG. 8 there is shown an alternative embodiment of the tool 100B constructed in accordance with this invention to also enable the loading of a stack or column of clips 20 therein. The embodiment of the tool 100B shown in FIG. 8 is identical to that of tool 100 shown in FIG. 1 except for the clip loading mechanism (as will be described hereinafter). Thus, in the interest of brevity only that portion of the tool 100B will be described.

As can be seen in FIG. 8 the body portion 102 of the tool 100B has a cartridge 172 mounted on the proximal end thereof. The cartridge 172 is a tubular member having a central passageway 174 which communicates with a central passageway 114A in the body portion 102. The passageway 114A is similar to passageway 114 of tool 100 except that it is of a larger internal diameter to accommodate a stack of cartridge loaded clips 20 therein. The distal end of the passageway 114A opens to the space between the swing jaws 106 and 108 to deposit the distal-most clip 20 of the stack of clips into that space. The pusher member 112 is located in the passageway 174.

When the cartridge is loaded, i.e., full of a stack of clips 20, the pusher member is located so that its distal end 116 is located proximally of the proximal-most clip of the stack of clips. The cartridge 172, with the stack of clips and pusher therein is then mounted onto the proximal end of the tool body 104 so that the passageway 174 in the cartridge is axially aligned with the passageway 114A in the tool body. The pusher 112 is then operated by pressing on its proximally located head 176 in the distal direction to push the stack of clips into the passageway 114A until the distal-most clip of the stack of clips is located in the space between the swing jaws 106 and 108.

The tool 100B is used in a similar manner as that described heretofore, with the most distally located clip being pushed out of the tool by the next successive clip under the force applied by the pusher member.

In FIG. 11 there is shown at 200 an alternative embodiment of a clip constructed in accordance with this invention. The clip 200 is arranged to be introduced into the body of the patient in a similar manner as that described heretofore, except for the use of a different delivery tool. In this regard the clip 200 is delivered and operated by tool 400 (FIG. 14), the details of which will be described after describing the construction of the clip 200.

As can be seen in FIGS. 11-13 the clip 200 is very similar in construction to a conventional "alligator" clip. Thus it includes a pair of jaws 202 and 204 which are pivotally connected together by a pivot pin 206. The pivot pin extends through aligned holes in a pair of tabs 208 located on each side of the jaw 202 at an intermediate point therealong. A similar pair of tabs 210 is located on each side of the jaw 204 at a similar intermediate point. The pair of tabs 210 are disposed between the pair of tabs 208.

The inner surface 212 contiguous with the distal end of each of the jaws 202 and 204 is serrated. These portions of the jaws define the "mouth" of the clip 200 therebetween. A torsion or compression spring 214 is interposed between the proximal ends 216 of the jaws 202 and 204. This spring applies a bias force to the proximal ends of the jaws to bias the distal ends of the jaws closed.

The clip 200 is arranged to be located within a bore or passageway 402A in the body 402 of the tool 400. A pusher member 112 (similar to that described heretofore) extends into the passageway 402A at the proximal end of the tool. The inner diameter of the passageway 402A is large enough to accommodate the clip 200 therein, but small enough to constrain the proximal ends 216 of the clip's jaws 202 and 204 toward each other so as to hold their distal ends apart (open) against the bias of the spring. The clip 200 is held in this orientation in the distal end of the tool 400, with the distal end 116 of the pusher member 112 abutting the proximal end of the clip.

Operation of the tool 400 and clip 200 will now be described. The distal end of the tool 400 with a clip 200 held therein is inserted into the percutaneous incision or puncture in a manner similar to that described heretofore. When the tool is at the desired position, e.g., adjacent an tissue or an organ like a gallbladder 22 (FIG. 11), the pusher member is operated to push the clip out of the distal end of the tool's body 402. When the clip has been moved to the position wherein its the proximal end has cleared the distal end of the tool's body, as shown in FIG. 12, whereupon the proximal ends of clip's jaws are no longer constrained by the passageway 402 so that the bias force of the spring 214 between those ends causes the clip's jaws to immediately snap closed. This action has the same effect as described heretofore to trap the tissue 24 within the clip's mouth without piercing it as shown in FIG. 13. The tool may then be withdrawn.

In FIG. 14 there is shown the entire tool 400 of FIGS. 11-13. In FIG. 20 there is shown an entire tool 400' which constitutes a slight modification of the tool 400. The tools 400 and 400' can also be used with the clips 500 and 500' (to be described later). The differences between the tools 400 and 400' will be considered later, with the common components of the tools 400 and 400' being given the same reference numerals in the interests of brevity.

As can be seen in FIG. 14 the proximal end of the tool 400 is constructed in a manner similar to a conventional "caulk-tube gun." In particular the tool 400 includes frame 404 including one extending handle member 406 having a finger hole 408 therein. A second handle or trigger member 410, having a finger hole 412 is pivotally mounted onto the frame by a pivot pin 414. When so mounted the finger holes 412 and 408 are adjacent each other, whereupon the surgeon can insert his/her thumb through hole 408 and his/her index finger through hole 412 to squeeze (pivot) the trigger 410 toward the handle 406.

At the upper end of the trigger is a pin 416 which is adapted to engage a disk-like member 418. The disk-like member 418 includes a central opening through which the proximal end portion of the pusher rod 212 extends. The disk-like member is arranged to frictionally engage the pusher rod 212 to slide it a predetermined distance in the distal direction each time that the trigger 410 is pivoted toward the handle 406.

A helical biasing spring 420 is located within an opening 422 in the frame 404 so that it bears against or biases the disk-like member 418 toward the rear (proximally). The pusher rod 212 extends through the spring 420. This arrangement insures that the pusher rod will not be moved in a distal direction until the trigger is operated.

A locking member 424 is pivotally mounted on the frame 404 by a pin 426, with a biasing spring 428 located between the locking member and the frame. The locking member includes a hole through which the pusher rod extends to frictionally engage the rod and thereby prevent it from moving in a proximal direction unless the locking member is pressed inward against the bias of the spring 428. This latter action is accomplished when it is desired to load the tool with a stack of clips (as will be described later).

The proximal end of the frame 404 includes a bayonet connector 430 which is arranged to engage a mating connector 432 on the tool body 402. The passageway 402A in the tool body 402 is arranged to hold a stack of clips therein. These clips can be of the type previously described and denoted by the reference numeral 200, or may be of the type denoted by the reference numeral 500 in FIG. 15 or of the type denoted by reference numeral 500' in FIG. 18. In FIG. 14 the tool 400 is shown with a stack of clips 500 therein. In either case the distal end of the pusher member 112 is arranged to be located immediately adjacent the proximal end of the most proximally located clip in the stack so that when the pusher rod is moved distally by the operation of the trigger the distally-most located clip is expelled from the tool to grasp the tissue 22 as described heretofore with reference to clip 200.

The loading of a stack of clips in the tool 400 is accomplished by securing a tool body 402 having a stack of clips within its passageway 402A to the frame portion 404. To that end the surgeon presses the locking member 424 toward the frame to release the frictional engagement of that member on the pusher rod. The pusher rod is then withdraw (moved proximally) until its distal end is located inside the bayonet connector 430 forming a portion of the frame 404. The tool body 402 having the stack of clips therein is then connected to the frame by engaging its bayonet connector 432 with the frame's bayonet connector 430.

The tool 400' is identical in all respects to that of tool 400, except that in lieu of the bayonet connectors 430 and 432 of the tool 400 the tool 400' makes use of a male luer lock 430 on the frame 404 and a female luer lock 432' on the body (tube) 402. In addition the tool 400' includes an end piece 212' on the proximal end of the pusher rod 212.

FIGS. 15-17 show the embodiment of the clip 500 mentioned heretofore. That clip is similar in construction and operation to clip 200. However, unlike clip 200 but like clip 20, clip 500 includes means which is actuatable to enable its mouth to be opened against the bias force tending to keep the mouth closed so that the tissue trapped within the mouth may be released when desired. Thus, as can be seen in FIGS. 15 the clip 500 basically comprises a pair of jaws 502 and 504 which are pivotally connected together by a pivot pin 506. The pivot pin extends through aligned holes in a pair of tabs 508 located on each side of the jaw 502 at an intermediate point therealong. A similar pair of tabs 510 is located on each side of the jaw 504 at a similar intermediate point. The pair of tabs 510 are disposed between the pair of tabs 508.

The distal end of each of the jaws 502 and 504 includes plural serrations forming teeth 512. These portions of the jaws define the "mouth" of the clip 500 therebetween. A torsion or compression spring (not shown in FIGS. 16 and 17 but shown at 503 in FIG. 19) is interposed between the proximal portions of the jaws 502 and 504. This spring applies a bias force to the proximal ends of the jaws to bias the distal ends of the jaws closed.

The proximal end of each of the jaws 502 and 504 terminates in an angularly extending projection 514. These projections form respective cam surfaces which are arranged to be engaged by the open distal end 402B of the tool body 402 to effect the opening of the clip's mouth to release tissue trapped therein as will be described later. A retraction filament or wire 516 is connected between the free ends of the projections 514 as shown in FIG. 15.

The clip 500 is arranged to be located within a bore or passageway 402A in the body 402 of the tool 400 (or tool 400' for that matter) as described earlier. The inner diameter of the passageway 402A is large enough to accommodate the clip 500 therein, but small enough to constrain the proximal ends of the clip's jaws 502 and 504 toward each other so as to hold their distal ends apart (open) against the bias of the spring. Each clip 500 in the stack is held in this orientation in the passageway 402A of the tool 400, with the distal end of the pusher member 112 abutting the proximal end of the proximally-most located clip.

Operation of the clip 500 is the same as described with reference to clip 200 and thus will not be reiterated herein.

Like the clips 20, each of the clips 200 and 500, includes a positioning tether 36 (not shown in the interest of drawing simplicity) arranged to be pulled as described heretofore to effect the desired tissue reflection. Thus, the clips 200 and/or 500 may be used in the same manner as described earlier with respect to clips 20, e.g., they may be coupled together via the tether in a pulley-like configuration. They may also include hammock-like retaining members like that described earlier for use in the same manner as that described earlier.

As mentioned earlier the clip 500, like clip 20, is arranged to be readily released from tissue which it has trapped. Thus, the following discussion will be directed to the operation of the clip 500 and the tool 400 to release trapped tissue from the mouth of the clip. Accordingly, when it is desired to release the clip 500 from tissue 22 it has trapped within its mouth the tool 400 is positioned so that the open distal end of its body 402 is located adjacent the proximal end of the clip 500 as shown in FIG. 15. A grabber member 434 is then extended outward from the passageway 402A in the tool 400 so that its hooked end 436 engages or hooks onto the filament or wire 516 extending between the proximal ends of the jaws of the clip. The grabber member 434 is then retracted within the passageway 402A of the tool's body. This action pulls the clip towards the tool and causes the portions of the tool's body contiguous with the entrance to the passageway 404A to ride or slide along the cam surfaces defined by the clip extensions 516, thereby squeezing the proximal ends of the clip's jaws 502 and 504 together and concomitantly opening the clip's mouth. Accordingly, the tissue portion 24 which had been trapped in the clip's mouth is now released. The clip may then be removed from the patient in a manner like that described earlier.

As mentioned earlier in FIG. 20 there is shown a system constructed in accordance with the teachings of this invention being used to effect the reflection of internally located tissue during a laparoscopic procedure, e.g., laparoscopic bowel resection. As is conventional in such procedures a laparoscope (not shown) is introduced, via a trocar (not shown), through the patient's umbilicus into the insufflated abdomen 10 to provide a visual image of the bowel to be resected. In accordance with the teachings of this invention plural clips 500' for securement to portions of the bowel or other tissue to be positioned by the surgeon, are introduced into the abdomen by use of the instrument 400'.

The instrument 400' is extended through a conventional trocar 14, e.g., a 5 mm trocar, into the patient's abdomen. The surgeon can manipulate the trocar 14 so that the open free end 402B of the instrument's clip delivery tube 402 is located adjacent a first portion of tissue 12 e.g., a section of bowel, which the surgeon wishes to reflect or otherwise position. Once that has been accomplished the instrument is operated to eject the distal-most clip 500' from the instrument 400' in the same manner as described heretofore, whereupon the clip 500' is freed of the instrument and its mouth closes on the immediately adjacent tissue portion to trap it therein. Once that tissue portion is trapped within the mouth of clip, and assuming that the surgeon deems it necessary to utilize another clip to effect the tissue reflection, the surgeon can attach a second clip 500' to another portion of the internally located tissue 12. To achieve that end the surgeon manipulates the trocar 14 through which the introducer instrument 400, extends in the desired direction so that the free end of the instrument's introducer tube 402 is aimed at the tissue portion to be grasped by clip 500'. The instrument 400' is then operated in the same manner as described heretofore to eject the next clip 500' from the stack into the abdomen, whereupon it traps the immediately adjacent tissue portion within its mouth. Depending upon the procedure being accomplished, other clips may be secured to different portions of the tissue to be reflected by merely directing the trocar 14 toward that tissue and operating the instrument 400' to secure the clips 500' to the tissue. If necessary, another trocar can be introduced at a different site and the instrument 400' inserted therethrough to place one or more clips through that trocar onto internally located tissue adjacent that trocar.

In order to expedite the expulsion/ejection of the clips 500' from the instrument 400' and to expedite the coupling of the positioning/holding means to those clips, the clips 500' of the embodiment of the invention shown in FIGS. 18, 19, 20, 21, and 24 are identical to the clips 500 except for a few structural differences. Thus, in the interests of brevity all common components of clips 500 and 500' are given the same reference numerals. The differences between the clips 500' and 500 is as follows. Each of the clips 500' includes two pair of stops 550 and 552. The stops of the pair 550 project perpendicularly from the sides of the proximal portion 514 making up jaw 502 of the clip 500, while the stops of the pair 552 project perpendicularly from the sides of the proximal portion 514 making up jaw 504 of the clip.

Figure 21:
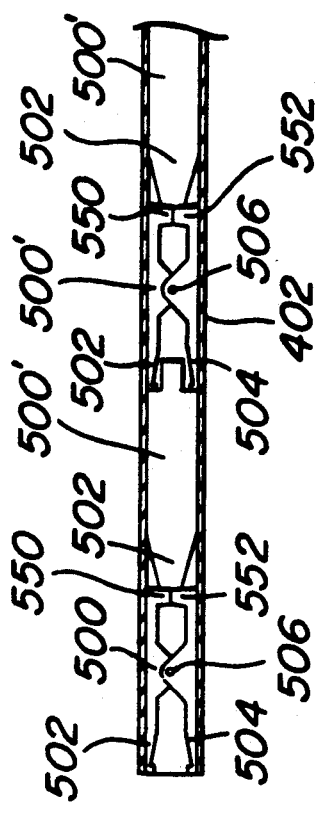
FIG. 21 is an enlarged sectional view of the distal end of the instrument shown in FIG. 20 holding a stack of clips like shown in FIG. 18 for introduction into the body of a being to clamp respective portions of tissue located therein.

In accordance with one aspect of this invention the clips 500' are stacked within the delivery tube 402 of instrument 400' so that alternate clips are oriented about the central longitudinal axis of the instrument at an angle of 90 degrees with respect to each other, whereupon the distal end of the open jaws 502 and 504 of one clip 500' engage the pairs of stops 550 and 55 of the immediately preceding (distally) located clip 500' as shown in FIG. 21. Accordingly, when the instrument 400' is operated the stack of clips 500' will push one another distally through the introducer tube 402 without the clips nesting up on each other, which action could cause misoperation of the clip ejection process.

Another difference between clips 500' and 500 is that each clip 500' includes a generally V-shaped retraction wire 554 secured to the proximal portion 514 of the clip in lieu of the filament or wire 516 described earlier. In particular, the ends 560 of the legs 556 and 558 making up the retraction wire 554 extend through respective holes in the proximal portions 514 and are crimped in place therein.

Once the clip(s) 500' have been secured to the internally located tissue 12, the surgeon is now ready to reflect that tissue to the desired position(s). For example, in order to reflect the tissue to which a particular clip 500' is secured to a desired position the surgeon selects an appropriate site on the skin covering the abdomen through which a positioning/holding device for releasable securement to the clip can be introduced. To that end and in accordance with one aspect of this invention, a very small diameter piercing device 700 (FIG. 20), e.g., a standard 13 gauge hypodermic needle, is used to form a very small percutaneous incision or puncture 702 through the skin 704 and abdominal wall 706 at the selected site on the abdomen. Similar devices 700 are used to form similar punctures at other sites for positioning clips located adjacent those other sites. The use of such small diameter devices 700, to form the percutaneous incisions or punctures 702 through which the clips positioning/holding devices are to be introduced (as will be described later) is desirable since such incisions or punctures are less invasive than those formed by a conventional 5 mm, or greater, trocar. Moreover, the incisions or punctures 702 are less traumatic to form, and in addition will automatically close without loss of abdomen insufflation and without requiring suturing when the device is removed.

Figure 22:
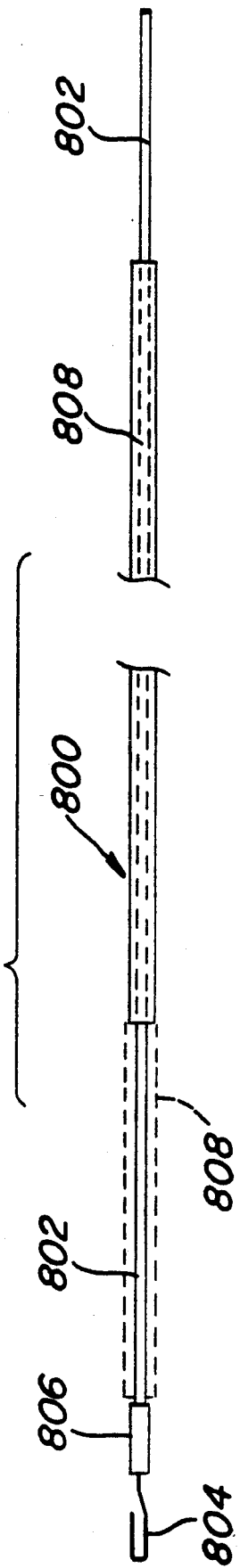
FIG. 22 is a plan view of a positioning element forming a portion of the system shown in FIG. 20 and constructed in accordance with this invention for releasable coupling to a clip attached to internally located tissue for effecting the reflection of such tissue from outside the body of said being.

Once each small percutaneous incision or puncture 702 is made by a respective needle 700, a respective positioning/holding device 800 constructed in accordance with this invention, is introduced through the associated needles 700. Each positioning/holding device is arranged to be coupled, e.g., releasably secured, a respective clip having a portion of the internally located tissue trapped within its mouth. Each positioning/holding device 80 is of identical construction and will now be described with reference to FIGS. 20 and 22. As can be seen therein the positioning/holding device is preferably in the form of a tension cable assembly basically comprising an elongated, flexible, braided, cable 802, e.g., stainless steel, having a distal end portion in the form of a blunt hook 804. The blunt hook is connected to the cable 802 via a coupling 806. An elongated, relatively rigid, e.g., stainless steel, sheath or sleeve 808 (FIG. 22) is slidable mounted on the cable 802 and is arranged to freely slide longitudinally therealong up to the coupling 806.

The external diameter of the tension cable assembly 800 is smaller than the internal diameter of the needle 700 through which it is introduced so that it can be freely extended therethrough, into the body of the being to the position adjacent a clip as shown in FIG. 20. In this position the hook 804 is located adjacent the clip, 500' while the slidable sheath 808 is located immediately adjacent the coupling 806, so that the distal portion of the sheath is located within the insufflated abdomen 10 and the proximal portion of the sheath is located outside of the body of the patient. The needle 700 may then be removed from the percutaneous incision or puncture 702 by sliding it in the proximal direction along the cable 802.

In order to grab the clip with the tension cable assembly 800, the surgeon grasps the outwardly extending proximal portion of the sheath 808 to manipulate (aim) it so that the blunt hook 804 catches onto the retraction wire 554 of the clip. In order to facilitate the securement of the hook to the clip the sheath 808 may include means (not shown) for holding it with respect to the cable 802 so that longitudinal and/or rotational movement of the sheath effects concomitant movement of the cable.

Once the hook of the cable has been secured to the clip, the sheath 808 is slid along the cable in the proximal direction away from the incision or puncture 702 to get it out of the way. In fact, the sheath 808 may be completely slid off of the cable 802. Whether or not the sheath is left in place on the cable is a function of the desires of the surgeon and depends upon the technique to be used to remove the clips and the tension cables from the patient after the laparoscopic procedure has been completed. In any event the movement of the sheath 808 away from the point at which the cable enters the percutaneous incision or puncture 702 into the patient's abdomen is most desirable to provide a relatively unobstructed working area for the surgeon.

After the sheath 808 has been slid out of the way the surgeon may then pull on an externally located portion of the flexible cable 802 to move the tissue 12 within the associated clip's mouth to a desired location toward the abdominal wall 706. When the surgeon is satisfied that the tissue is in the desired position the surgeon fixes the cable 802 in place with respect to the patient's body by any suitable means. In the embodiment shown in FIG. 20 a strip of adhesive tape 810 is used to secure a portion of the flexible cable 802 of each clip positioning device to the skin of the patient adjacent the percutaneous incision or puncture through which the cable extends. Each cable may be fixed in place by other means, e.g., a standard needle holder, a clamp, hemostat, etc. (not shown).

As should be appreciated by those skilled in the art the fixing of the various positioning devices in place on the abdomen frees the surgeon or other operating room personnel for performing tasks other than holding the reflected tissue in place (as has characterized prior art laparoscopic surgical procedures, wherein the surgeon or other personnel have the hold the various tissue grasping devices in position while the surgeon carries out the procedure).

In accordance with a preferred aspect of this invention the combined length of the blunt hook 804, the coupling 806, and clip 500' is very short, e.g., 0.9 inch (2.29 cm) or less, to enable the tissue 12 trapped in the clip's mouth to be reflected much closer to the abdominal wall than that possible with prior art retracting instruments (since such instruments are used through trocars which typically extend three to four inches into the body of the being).

When it is desired to release the reflected tissue 12, such action can be accomplished in several ways. For example, one technique for releasing the reflected tissue is to release, e.g., untape, the associated cable 802 from the patient's body, and slide the sheath 808 (which had been left on a proximal portion of the cable remote from the percutaneous incision or puncture 702) in the distal direction back through the incision or puncture until the distal end portion of the sheath is immediately adjacent the coupling 806. The surgeon may then manipulate the sheath 808 and cable to unhook the blunt hook 804 from the retraction wire 554 of the clip 500', thereby releasing the reflected tissue (albeit it with the clip still connected thereto). The tension cable assembly 800 may then be extracted from the body of the patient by pulling on it in the proximal direction through the same incision or puncture 702 through which it was introduced.

In order to facilitate the extraction of the tension cable assembly as just described it may be desirable to modify the coupling 806 so that it is positionable with respect to the blunt hook 804 so that it overlies or covers the free end portion of the blunt hook, to prevent that portion from snagging on the tissue of the patient contiguous with the incision or puncture 702.

Another technique for releasing the reflected tissue is accomplished by removing the sheath 808 from the tension cable assembly. Then the tension cable assembly is released by untaping the cable 802 from the patient's abdomen, whereupon the tissue 12 to which the clip and tension cable are connected will move to some neutral internal position, carrying the clip and cable with it, and thereby releasing the tension on the cable. Such action may result in the automatic disconnection of the tension cable's blunt hook 504 from the clip's retraction wire 554. If not, the surgeon may manipulate the cable 802 slightly to effect that disconnection. The tension cable may then be removed from the body of the patient by extending a retraction tool (like that to be described later) through the trocar 14 to engage (e.g., hook onto) the blunt hook 804 of the tension cable. Once that has been accomplished the tension cable can then be withdraw through the trocar 14 out of the patient's body.

If desired clips in accordance with this invention may be formed of any suitable material, e.g., a resorbable polymer, so that they may be left within the body of the patient after the laparoscopic procedure has been accomplished and the tension cable assemblies removed. If, however, removal of the clips from the patient's body is desired such action may be readily accomplished by use of a clip removal tool constructed in accordance with is invention. One such tool 900 is shown in FIG. 23.

As can be seen in FIGS. 23 and 24, the tool 900 basically comprises small diameter, e.g., 0.185 inch (4.7 mm), elongated tube 902 terminating at a handle 904 at the proximal end thereof. The distal end 906 of the tube is open. An elongated wire 908 extends longitudinally through the tube 902. The distal end of the wire is in the form of a blunt hook 910. A slidable plug 912 having a central hole 914 through which the wire 908 extends is located adjacent the blunt hook 910. The wire 908 is arranged to be slid longitudinally down the tool to move the blunt hook from the retracted position (wherein it is located within the distal free end of 906 the tube 902 as shown in full in FIG. 23) to an extended position (wherein it is located outside of the free end of the tube as shown in phantom therein). To that end the proximal end of the wire 902 is fixedly secured to a shaft 916 portion of a thumb cap 918. The shaft portion 916 extends through the portion of the tube 902 within the handle 904. A stop member 920 is fixedly secured within the tube adjacent the handle 903 and includes a central opening 922 through which the wire 908 extends. A helical compression spring 924 is interposed between the stop member 920 and the free end of the thumb cap shaft 916 to bias the thumb cap and the wire 900 attached thereto in the proximal direction to the retracted position. When the thumb cap is pressed inward (distally) with respect to the handle 904 and the bias force of the spring 924 is overcome the wire 908 is moved proximally so that its blunt hook 910 is in the extended position located outside the distal end 906 of the tool 900.

Operation of the retraction tool 900 to effect the removal of a clip 500' is as follows. The retraction tool is introduced through the trocar 14 and the trocar aimed so that the open free end 906 of the retraction tool 900 is located within the abdomen adjacent a clip 500' to be removed. The surgeon then presses on the thumb cap 918 to extend the hook 910 to the extended position so that it catches the V-shaped retraction wire 554 of the clip. Once this has been accomplished the thumb cap 918 is released, whereupon the hook 910, with the clip now connected to it, is pulled into the open end 906 of the retraction tool tube 902. This action causes inner surface portions of the tube at the free end thereof to ride over the legs 556 and 558 making up the V-shaped retraction wire 554. Accordingly, the proximal ends 514 of the clips jaws 502 and 504 begin to move toward each other, thereby initiating the opening of the clip's mouth. Continued retraction of the clip 500' into the open free end of the retraction tool causes the inner surface portions of the tube at the free end thereof to ride over the cam surfaces formed by angularly extending projections 514 of the proximal portions of the clip's jaws, thereby further opening of the clip's mouth, whereupon the tissue which had been trapped in the clip's mouth is released, leaving the clip partially within the tool as shown in FIG. 24. The tool 900 with the clip therein may then be removed from the patient's body through the trocar 14. Every other clip can be removed in the same manner.

It should be pointed out at this juncture that other instruments, tools, devices, and clips than that described heretofore can be constructed in accordance with the teachings of this invention. Moreover the methods of use described are not the only methods which can be effected by use of such device. For example, the clips of this invention can be used for purposes other than tissue reflection or positioning, e.g., they may be used to secure some device or member to a portion of internally located tissue. Moreover, the apparatus and methods are not limited to laparoscopic, endoscopic or other minimally invasive surgery, and can thus be used for open surgery as well. Thus, it must be kept in mind that, the structures and methods of use as described heretofore are merely exemplary.

Without further elaboration the foregoing will so fully illustrate out invention that others may, by applying current or future knowledge, adopt the same for use under various conditions of service.

We claim:

1. A kit for reflecting tissue located within the body of a being via a small percutaneous incision or puncture, said kit comprising at least one clip means, an introducer instrument, and clip positioning mans, said introducer instrument being of a small diameter holding said clip means therein and insertable through a small percutaneous incision or puncture in the body of said being to deliver said clip means therethrough to the situs of said tissue, said introducer instrument including means operable from outside the body of said being for releasing said clip means from said introducer instrument so that said clip means is free of said introducer instrument, said clip means comprising a pair of jaws and biasing means, said jaws defining a mouth therebetween and being moveable between a first orientation wherein said jaws are disposed apart and a second orientation wherein said jaws are disposed closer together, said biasing means being coupled to said jaws and being actuatable from outside the body of said being to move said jaws from said first orientation to said second orientation so that at least a portion of said tissue is trapped within said mouth of said clip means, said clip positioning means having a first portion and a second portion, and being extendable through a small percutaneous incision or puncture in the body of said being from outside the body of said being so that said first potion is coupled to said clip means and said second portion is located outside of the body of said being, said second portion being engagable outside the body of said being to draw on said clip positioning means, whereupon said portion of tissue trapped within the mouth of said clip means is moved to a desired position within the body of said being.

2. The kit of claim 1 wherein said introducer instrument is arranged for introducing plural clip means through said small percutaneous incision or puncture through which said introducer instrument is inserted.

3. The kit of claim 1 wherein said clip positioning means comprises a generally flexible, elongated member, and wherein said first portion of said positioning means comprises connecting means for connection to said clip means.

4. The kit of claim 3 wherein said clip positioning means is arranged for releasable connection to said clip means.

5. The kit of claim 4 wherein said clip positioning means includes hook means.

6. The kit of claim 3 wherein said clip positioning means additionally comprises substantially rigid, slidable sleeve means disposed on said flexible member.

7. The kit of claim 6 wherein said clip positioning means is arranged for releasable connection to said clip means.

8. The kit of claim 7 wherein said clip positioning means includes hook means.

9. The kit of claim 3 wherein said introducer instrument is inserted through a first small percutaneous incision or puncture in the body of said being, and wherein said system additionally comprising small diameter passageway means arranged to be located within a second percutaneous incision or puncture in the body of said being, said small diameter passageway means being arranged for receipt of said clip positioning means therethrough.

10. The kit of claim 9 wherein said passageway means comprises a piercing needle.

11. The kit of claim 1 additionally comprising fixing means for fixing the position of said clip positioning means with respect to the body of said being.

12. The kit of claim 11 wherein said fixing means is arranged to be releasably secured to said clip positioning means outside the body of said being and adjacent the percutaneous incision or puncture through which the clip positioning means extends.

13. The kit of claim 12 wherein said positioning means comprises a generally flexible member to which said clip fixing means is arranged to be releasably secured, and wherein said first portion of said clip positioning means comprises connecting means for connection to said clip means.

14. The kit of claim 13 wherein said connecting means is arranged for releasably connection to said clip means.

15. The kit of claim 14 wherein said connecting means includes hook means.

16. The kit of claim 13 wherein said clip positioning means additionally comprises substantially rigid, slidable sleeve means disposed on said flexible member.

17. The kit of claim 16 wherein said clip positioning means is arranged for releasable connection to said clip means.

18. The kit of claim 17 wherein said clip positioning means includes hook means.

19. The kit of claim 1 additionally comprising release means arranged to introduce into the interior of the body of said being via a percutaneous incision or puncture to the situs of said clip means, for causing said clip means to release said first portion of said tissue from the mouth of said clip means.

20. The kit of claim 19 wherein said release means is arranged to retract said clip means through said incision or puncture out of the body of said being.

21. The kit of claim 1 wherein said means operable from outside the body of said being for releasing said clip means also actuates said biasing means to move said jaws from said first orientation to said second orientation.

22. A kit for effecting the positioning of a first portion of tissue located within the body of a being via a small percutaneous incision or puncture, said system comprising at least one clip, positioning means for said clip, and an introducer instrument, said introducer instrument being of a small diameter holding said clip therein and insertable through a small percutaneous incision or puncture in the body of said being to deliver said at least one clip therethrough to the situs of said first portion of tissue, said introducer instrument including means operable from outside the body of said being to free said clip therefrom when said clip is within the body of said being, said clip comprising a pair of jaws and biasing means, said jaws having portions defining a mouth therebetween, said jaws being moveable between a first orientation wherein said portions of said jaws are disposed apart and a second orientation wherein said portions of said jaws are disposed closer together, said biasing means being coupled to said jaws and being actuatable from outside the body of said being, whereupon said jaws move from said first orientation to said second orientation so that a portion of said tissue is trapped within said mouth of said clip, said positioning means having a first portion and as second portion, said positioning means being extendable through a small percutaneous incision or puncture in the body of said being so that said first portion is coupled to said clip and said second portion is located outside of the body of said being, said second portion of said positioning means being engagable outside the body of said being to locate and hold said positioning means in a desired position, whereupon said portion of tissue trapped within said mouth of said clip is held at a desired position within the body of said being.

23. The kit of claim 22 wherein said instrument includes means to effect the actuation of said biasing means.

24. The kit of claim 23 wherein said biasing means is resettable to enable said jaws to move to said first orientation so that said first portion of said tissue is released from said mouth.

25. The kit of claim 24 wherein said instrument includes means for resetting said biasing means.

26. The kit of claim 24 additionally comprising a tool insertable through a small percutaneous incision or puncture in the body of said being for resetting said biasing means.

27. The kit of claim 26 wherein said biasing means comprises a resilient member interposed between said jaws for biasing said portions of said jaws to said second orientation.

28. The kit of claim 27 additionally comprising cooperating means, and wherein said biasing means additionally comprises cam means engagable by said cooperating means, said cooperating means being movable along said cam means to a first point to reset said biasing means, whereupon said portions of said jaws assume said first orientation against the bias of said resilient member.

29. The kit of claim 28 wherein said cooperating means is movable relative to said cam means to a second point wherein said biasing means is actuated.

30. The kit of claim 29 wherein said cooperating means comprises cam means forming a part of said instrument.

31. The kit of claim 23 wherein said biasing means comprises a resilient member interposed between said jaws for biasing said portion of said jaws to said second orientation.

32. The kit of claim 31 additionally comprising means, and wherein said biasing means additionally comprises cam means engagable by said cooperating means, said cooperating means being movable along said cam means to a first point to reset said biasing means, whereupon said portions of said jaws assume said first orientation against the bias of said resilient member.

33. The kit of claim 32 wherein said cooperating means is movable relative to said cam means to a second point wherein said biasing means is actuated.

34. The kit of claim 23 wherein said instrument comprises a hollow member for holding said clip therein.

35. The kit of claim 24 wherein said instrument comprises a pusher member for ejecting said clip therefrom.

36. The kit of claim 34 wherein said instrument comprises a pair of swing jaws having means for actuating said biasing means.

37. The kit of claim 23 wherein said instrument comprises a pusher member for ejecting said clip therefrom.

38. The kit of claim 37 wherein said instrument comprises a pair of swing jaws having cooperating means for actuating said biasing means.

39. The kit of claim 38 wherein said biasing means comprises a resilient bridging section connecting said jaws of said clip for biasing said portions of said jaws to said second orientation.

40. The kit of claim 39 wherein said biasing means additionally comprises cam means arranged to be engaged by said cooperating means, said cooperating means being arranged to move along said cam means to a first point thereon as said clip is ejected from said instrument to reset said biasing means, whereupon said portions of said jaws assume said first orientation against the bias of said resilient bridging section.

41. The kit of claim 40 wherein said cooperating means is arranged to move along said cam means to a second point as said clip is ejected from said instrument to actuate said biasing means.

42. The kit of claim 41 wherein said swing jaws are moveable to enable said instrument to engage said clip after said clip has trapped said tissue within said mouth to set said biasing means wherein said portions of said jaws are again in said first orientation.

43. The kit of claim 23 wherein said instrument comprises a pair of swing jaws having means for actuating said biasing means.

44. The kit of claim 23 wherein said positioning means comprises a tether.

45. The kit of claim 44 additionally comprising another clip for trapping a second portion of said tissue within the mouth thereof, with said tether of one of said clips being coupled to the other of said clips to form a pulley arrangement.

46. The kit of claim 23 wherein said positioning means comprises a web of material for covering a third portion of tissue, said third portion of tissue being located adjacent said first portion of said tissue.

47. The kit of claim 46 additionally comprising another clip for trapping a second portion of said tissue within the mouth thereof, said clips being connected to each other by said web to form hammock means, said hammock means covering and holding said third portion of said tissue, said third portion of said tissue also being located adjacent said second portion of said tissue.

48. The kit of claim 22 wherein said biasing means comprises a spring.

49. The kit of claim 22 wherein said biasing mans is resettable to enable said jaws to move to said first orientation so that said first portion of said tissue is released from said mouth.

50. The kit of claim 22 wherein said biasing means comprises a resilient member interposed between said jaws and biasing said portions of said jaws to said second orientation.

51. The kit of claim 50 additionally comprising cooperating means, and wherein said biasing means additionally comprises cam means engagable by said cooperating means, said cooperating means being movable along said cam means to a first point to reset said biasing means, whereupon said portions of said jaws assume said first orientation against the bias of said resilient member.

52. The kit of claim 51 wherein said cooperating means is movable relative to said cam means to a second point wherein said biasing means is actuated.

53. The kit of claim 22 wherein said positioning means comprises a tether.

54. The kit of claim 53 additionally comprising another clip for trapping a second portion of said tissue within the mouth thereof, with said tether of one of said clips being coupled to the other of said clips to form a pulley arrangement.

55. The kit of claim 22 wherein said positioning means comprises a web of material for covering a third portion of tissue, said third portion of tissue being located adjacent said first portion of said tissue.

56. The kit of claim 55 additionally comprising another clip for trapping a second portion of said tissue within the mouth thereof, said clips being connected to each other by said web to form hammock means, said hammock means covering and holding said third portion of said tissue, said third portion of said tissue also being located adjacent said second portion of said tissue.

57. The kit of claim 22 wherein said biasing means additionally comprises cam means arranged to be engaged by cooperating means, said cooperating means being arranged to move relative to said cam means to a first point to reset said biasing means, whereupon said portions of said jaws assume said first orientation against the bias of said biasing means.

58. The kit of claim 57 wherein each of said jaws includes a distal portion and a proximal portion, said mouth of said clip being formed by said distal portions of said jaws, said cam means being located adjacent said proximal portions of said jaws.

59. The kit of claim 58 wherein said cam means comprise angularly extending free ends of said proximal portions of said jaws.

60. The kit of claim 58 wherein said biasing means biases said proximal portions of said jaws away from each other, while biasing said distal portions of said jaws towards each other.

61. The kit of claim 57 wherein said biasing means biases said proximal portions of said jaws away from each other, while biasing said distal portions of said jaws towards each other.

62. The kit of claim 22 wherein said means operable from outside the body of said being for releasing said clip means also actuates said biasing means to move said jaws from said first orientation to said second orientation.

63. A method for reflecting tissue located within the body of a being by use of a clip means and clip positioning means, the method comprising providing at least one clip means having a pair of jaws and biasing means, said jaws having portions defining a mouth therebetween and being moveable between a first orientation wherein said jaws are disposed apart and a second orientation wherein said jaws are disposed closer together, said biasing means being coupled to said jaws and being actuatable to move said jaws from said first orientation to said second orientation, and providing an instrument having at least one of said clip means therein, inserting said instrument and said clip means through a small first percutaneous incision or puncture in the body of said being to a location adjacent said tissue, expelling said clip means from said instrument to free said clip means therefrom, actuating said biasing means to cause said jaws of said clip means to move to said second orientation so that a portion of said tissue is trapped within said mouth of said clip means, providing clip positioning means, and extending said clip positioning means through a percutaneous incision or puncture in the body of said being so that a first portion of said clip positioning means is coupled to said clip means and a second portion of said clip positioning means is located outside the body of said being, and manipulating said second portion of said clip positioning means from outside of the body of said being to effect the reflection of said tissue.

64. The method of claim 63 wherein said introducing instrument is inserted through a first small percutaneous incision or puncture in the body of said being, and wherein plural clip means are inserted through said first percutaneous incision or puncture for securement to respective portions of said tissue.

65. The method of claim 64 wherein said clip positioning means is extended through a second percutaneous incision or puncture in the body of said being.

66. The method of claim 63 wherein said clip positioning means is extended through a second percutaneous incision or puncture in the body of said being.

67. The method of claim 63 additionally comprising fixing said clip positioning means to the body of said being adjacent the percutaneous incision or puncture through which said clip positioning means extends.

68. The method of claim 67 wherein said introducing instrument is inserted through a first small percutaneous incision or puncture in the body of said being, and wherein said clip positioning means is extended through a second percutaneous incision or puncture in the body of said being.

69. The method of claim 63 wherein said clip positioning means includes a flexible member and substantially rigid sleeve means located thereon, and wherein said method comprises manipulating said sleeve means to direct said first portion of said clip positioning means toward said clip means so that it may be coupled thereto.

70. The method of claim 69 additionally comprising fixing said clip positioning means to the body of said being adjacent the percutaneous incision or puncture through which said clip positioning means extends.

71. The method of claim 69 additionally comprising sliding said sleeve means away from the percutaneous incision or puncture through which said clip positioning means extends.

72. The method of claim 71 additionally comprising fixing said clip positioning means to the body of said being adjacent the percutaneous incision or puncture through which said clip positioning means extends.

73. The method of claim 63 wherein said step of expelling said clip means from said instrument actuates said biasing means to cause said jaws to move to said second orientation.

74. A method for dynamically clamping a first portion of tissue located within the body of a living being comprises providing a clip having a pair of jaws and biasing means, said jaws having portions defining a mouth therebetween, said jaws being moveable between a first orientation wherein said portions of said jaws are disposed apart and a second orientation wherein said portions of said jaws are disposed closer together, said biasing means being coupled to said jaws and being actuatable, whereupon when said biasing means is actuated said jaws move substantially instantaneously from said first orientation to said second orientation, said clip being of a sufficiently small size to pass through a small percutaneous incision or puncture in the body of said being, and providing an instrument for releasably holding said clip therein, inserting said instrument and said clip through said incision or puncture so that said portions of said jaws are located immediately adjacent said first portion of said tissue, releasing said clip from said instrument, actuating said biasing means from outside the body of said being to cause said jaws to immediately move to said second orientation so that a portion of said tissue is trapped within said mouth, and providing positioning means not part of said instrument through a small percutaneous incision or puncture in the body of said being so that a portion of said positioning means is coupled to said clip and a portion of said positioning means is located outside the body of said being.

75. The method of claim 74 wherein said positioning means comprises tether means, said method comprising causing said tether means to extend from said clip through said small percutaneous incision or puncture to be readily accessible for drawing thereon to effect the movement of said first portion of said the tissue.

76. The method of claim 74 additionally comprising inserting said clip through a small percutaneous incision or puncture to trap a second portion of internally located tissue in the mouth of said other clip, coupling the tether means of one of said clips to the other of said clips to form a pulley arrangement.

77. The method of claim 74 wherein said clip additionally comprises a web of material, said method additionally comprising manipulating said device so that said web of material covers a portion of tissue adjacent said first portion of said tissue.

78. The method of claim 77 additionally comprising inserting another clip through a small percutaneous incision or puncture to trap a second portion of internally located tissue in the mouth of said other clip, coupling the web of said one of said clips to the other of said clips to form a hammock for covering and holding tissue adjacent said first and second portions of said tissue.

79. The method of claim 74 wherein said positioning means comprises a member which is arranged to be coupled to said clip, said member being extended through a percutaneous incision or puncture to provide a portion thereof outside of the body of said being, said method additionally comprising manipulating said member by said outside portion to effect the positioning of said tissue.

80. The method of claim 79 wherein said member comprises an elongated flexible element and wherein said method comprises drawing on said element in a proximal direction from outside of the body of said being.

81. The method of claim 80 wherein said percutaneous incision or puncture through which is a positioning means extends is a different percutaneous incision or puncture than that through which said clip is inserted.

* * * * *